US012582391B2

(12) United States Patent
Rolando et al.

(10) Patent No.: US 12,582,391 B2
(45) Date of Patent: Mar. 24, 2026

(54) INTERSEPTAL OCCLUDER DEVICE

(71) Applicant: Recross Cardio Inc., Dover, DE (US)

(72) Inventors: Giovanni Rolando, Dover, DE (US);
Thomas Gerhardt, Cape Town (ZA);
Marco Ferrone, Dover, DE (US);
Gilberto Melnick, Dover, DE (US)

(73) Assignee: Recross Cardio Inc., Dover, DE (US)

( * ) Notice: Subject to any disclaimer, the term of this
patent is extended or adjusted under 35
U.S.C. 154(b) by 350 days.

(21) Appl. No.: 18/251,383

(22) PCT Filed: Oct. 29, 2021

(86) PCT No.: PCT/IB2021/060023
§ 371 (c)(1),
(2) Date: May 2, 2023

(87) PCT Pub. No.: WO2022/091018
PCT Pub. Date: May 5, 2022

(65) Prior Publication Data
US 2024/0016487 A1    Jan. 18, 2024

(30) Foreign Application Priority Data

Nov. 2, 2020    (IT) ........................ 102020000026065

(51) Int. Cl.
A61B 17/00 (2006.01)
(52) U.S. Cl.
CPC .... A61B 17/0057 (2013.01); A61B 17/00234
(2013.01); A61B 2017/00243 (2013.01); A61B
2017/00575 (2013.01)
(58) Field of Classification Search
CPC ........... A61B 2017/00597; A61B 2017/00592;
A61B 2017/00606
See application file for complete search history.

(56) References Cited

U.S. PATENT DOCUMENTS

| | | | |
|---|---|---|---|
| 4,007,743 A | 2/1977 | Blake | |
| 4,964,850 A | 10/1990 | Bouton | |

(Continued)

FOREIGN PATENT DOCUMENTS

| | | |
|---|---|---|
| AU | 4352497 | 4/1998 |
| CN | 1736346 | 2/2006 |

(Continued)

OTHER PUBLICATIONS

International Search Report and Written Opinion issued in PCT
Application No. PCT/IB2021/060023, dated Feb. 8, 2022, in 14
pages.

*Primary Examiner* — Alexander J Orkin
(74) *Attorney, Agent, or Firm* — Knobbe, Martens, Olson
& Bear, LLP

(57)    ABSTRACT

The present invention relates to an occluder device (1)
comprising a supporting structure (2) said supporting struc-
ture (2) comprising a central portion (201) having a distal
end (202) and a proximal end (203); said supporting struc-
ture (2) comprising distal branches (204) extending away
from said distal end (202) of the central portion (201); said
supporting structure (2) comprising proximal branches (205)
extending away from said proximal end (203) of the central
portion (201); said proximal and distal branches (204, 205)
defining elastic hooked struts which are rotatable away from
the central portion (201) to anchor a septum (7) of a heart
(103); said occluder device (1) further comprising at least
one membrane (8); said membrane (8) comprises a mem-
brane body (11) connected to the distal or proximal branches
(204; 205); when the branches (204, 205) are in the unfolded
or lying position, said membrane (8) has a closed position
where the membrane (8) is in a configuration which provides
maximum occlusion to the supporting structure (2); wherein
said membrane (8) comprises at least one slit (21); which,
when actively engaged by an external device (108) the (Continued)

membrane (8) deforms the slit (21) which extends elastically, creating a passage lumen (27) for said external device (108).

19 Claims, 24 Drawing Sheets

(56) References Cited

U.S. PATENT DOCUMENTS

| | | | |
|---|---|---|---|
| 5,108,420 | A | 4/1992 | Marks |
| 5,425,744 | A | 6/1995 | Fagan et al. |
| 6,171,329 | B1* | 1/2001 | Shaw .................. A61B 17/0057 |
| | | | 606/151 |
| 6,206,907 | B1 | 3/2001 | Marino et al. |
| 6,379,368 | B1 | 4/2002 | Corcoran et al. |
| 6,712,836 | B1* | 3/2004 | Berg ................... A61B 17/0057 |
| | | | 606/213 |
| 7,665,466 | B2 | 2/2010 | Figulla et al. |
| 7,842,069 | B2 | 11/2010 | Widomski et al. |
| 8,277,482 | B2 | 10/2012 | Hruska et al. |
| 8,323,312 | B2 | 12/2012 | Clark |
| 8,752,258 | B2 | 6/2014 | Finch et al. |
| 8,870,913 | B2 | 10/2014 | Opolski et al. |
| 9,179,899 | B2 | 11/2015 | Freudenthal |
| 9,332,976 | B2 | 5/2016 | Yribarren |
| 9,414,823 | B2 | 8/2016 | Ben Hamou et al. |
| 9,456,812 | B2 | 10/2016 | Finch et al. |
| 9,532,772 | B2 | 1/2017 | Moszner et al. |
| 9,554,783 | B2 | 1/2017 | Pavcnik et al. |
| 9,840,577 | B2 | 12/2017 | Singhal et al. |
| 9,877,710 | B2 | 1/2018 | Amplatz et al. |
| 9,937,036 | B2 | 4/2018 | Sugimoto et al. |
| 10,265,059 | B2 | 4/2019 | Rowe et al. |
| 11,259,789 | B2 | 3/2022 | Rowe et al. |
| 2001/0039450 | A1 | 11/2001 | Pavcnik et al. |
| 2002/0042565 | A1 | 4/2002 | Cooper |
| 2003/0070682 | A1 | 4/2003 | Wilson |
| 2004/0143291 | A1* | 7/2004 | Corcoran ........... A61B 17/0057 |
| | | | 606/151 |
| 2004/0143292 | A1* | 7/2004 | Marino .............. A61B 17/0057 |
| | | | 606/151 |
| 2004/0143294 | A1* | 7/2004 | Corcoran ........... A61B 17/0057 |
| | | | 606/213 |
| 2005/0027261 | A1 | 2/2005 | Weaver |
| 2005/0113868 | A1 | 5/2005 | Devellian et al. |
| 2005/0171489 | A1 | 8/2005 | Weaver |
| 2005/0267524 | A1 | 12/2005 | Chanduszko |
| 2005/0288706 | A1* | 12/2005 | Widomski ....... A61B 17/12136 |
| | | | 606/213 |
| 2007/0073337 | A1 | 3/2007 | Abbott et al. |
| 2008/0033478 | A1 | 2/2008 | Meng |
| 2008/0051830 | A1 | 2/2008 | Eidenschink |
| 2008/0077180 | A1 | 3/2008 | Kladakis et al. |
| 2008/0147111 | A1* | 6/2008 | Johnson ................ A61F 2/0103 |
| | | | 606/200 |
| 2009/0177187 | A1 | 7/2009 | Weaver |
| 2010/0057192 | A1 | 3/2010 | Celermajer |
| 2010/0222810 | A1 | 9/2010 | Debeer et al. |
| 2011/0082495 | A1 | 4/2011 | Ruiz |
| 2011/0224720 | A1 | 9/2011 | Kassab et al. |
| 2011/0306916 | A1 | 12/2011 | Nitzan |
| 2012/0053686 | A1 | 3/2012 | McNamara |
| 2012/0150218 | A1 | 6/2012 | Sandgren et al. |
| 2012/0253386 | A1 | 10/2012 | Rowe |
| 2012/0265296 | A1 | 10/2012 | McNamara et al. |
| 2013/0073029 | A1* | 3/2013 | Shaw .............. A61B 17/12172 |
| | | | 623/1.36 |
| 2013/0190861 | A1 | 7/2013 | Chau et al. |
| 2014/0012368 | A1 | 1/2014 | Sugimoto et al. |
| 2014/0074155 | A1 | 3/2014 | Rothstein et al. |
| 2014/0107618 | A1 | 4/2014 | Hamboly |
| 2014/0163449 | A1 | 6/2014 | Rottenberg et al. |
| 2014/0194971 | A1 | 7/2014 | McNamara |
| 2014/0309684 | A1 | 10/2014 | Al-Qbandi et al. |

| | | | |
|---|---|---|---|
| 2015/0201945 | A1 | 7/2015 | Wojay |
| 2015/0216653 | A1 | 8/2015 | Freudenthal |
| 2015/0315399 | A1 | 11/2015 | Bredt et al. |
| 2016/0022423 | A1 | 1/2016 | McNamara et al. |
| 2016/0220357 | A1 | 8/2016 | Anand |
| 2016/0262768 | A1* | 9/2016 | Haverkost .......... A61B 17/0057 |
| 2016/0296684 | A1 | 10/2016 | Tamburino |
| 2017/0014115 | A1 | 1/2017 | Rafiee et al. |
| 2017/0079630 | A1 | 3/2017 | Xie et al. |
| 2017/0224323 | A1 | 8/2017 | Rowe et al. |
| 2017/0231766 | A1 | 8/2017 | Hariton et al. |
| 2018/0333150 | A1 | 11/2018 | Bak-Boychuk et al. |
| 2018/0339141 | A1* | 11/2018 | Scheule ................ A61M 39/24 |
| 2019/0099589 | A1 | 4/2019 | Walsh |
| 2019/0328374 | A1 | 10/2019 | Hendsbee |
| 2020/0368505 | A1 | 11/2020 | Nae et al. |
| 2021/0059684 | A1 | 3/2021 | Meyer et al. |
| 2022/0175364 | A1 | 6/2022 | Rowe et al. |
| 2022/0183694 | A1 | 6/2022 | Pan et al. |
| 2022/0211361 | A1 | 7/2022 | Rolando et al. |

FOREIGN PATENT DOCUMENTS

| | | |
|---|---|---|
| CN | 104042257 | 9/2014 |
| CN | 104224246 | 12/2014 |
| CN | 104414692 | 3/2015 |
| CN | 105054980 | 11/2015 |
| CN | 107397561 | 11/2017 |
| CN | 108451570 | 8/2018 |
| CN | 108714038 | 10/2018 |
| DE | 4222291 | 1/1994 |
| DE | 102005053958 | 5/2007 |
| DE | 102010019365 | 6/2011 |
| DE | 102014006984 | 11/2015 |
| EP | 0 653 921 | 5/1995 |
| EP | 0 655 222 | 6/1998 |
| EP | 0 541 063 | 9/1998 |
| EP | 0 545 091 | 7/1999 |
| EP | 0 861 049 | 4/2001 |
| EP | 1 149 561 | 10/2001 |
| EP | 1 210 014 | 6/2002 |
| EP | 1 474 043 | 11/2004 |
| EP | 1 509 144 | 3/2005 |
| EP | 0 888 083 | 6/2005 |
| EP | 1 538 994 | 6/2005 |
| EP | 1 595 504 | 11/2005 |
| EP | 1 641 400 | 4/2006 |
| EP | 1 670 345 | 6/2006 |
| EP | 1 673 132 | 6/2006 |
| EP | 1 018 943 | 10/2006 |
| EP | 1 737 349 | 1/2007 |
| EP | 0 947 165 | 7/2007 |
| EP | 1 718 213 | 7/2007 |
| EP | 0 876 793 | 12/2007 |
| EP | 1 928 327 | 6/2008 |
| EP | 1 948 037 | 7/2008 |
| EP | 1 965 706 | 9/2008 |
| EP | 1 605 865 | 12/2008 |
| EP | 1 836 969 | 6/2009 |
| EP | 1 765 180 | 11/2009 |
| EP | 2 140 815 | 1/2010 |
| EP | 2 066 241 | 6/2010 |
| EP | 2 056 723 | 7/2010 |
| EP | 1 955 661 | 3/2011 |
| EP | 1 842 490 | 9/2011 |
| EP | 2 427 123 | 3/2012 |
| EP | 2 528 646 | 12/2012 |
| EP | 2 029 029 | 3/2013 |
| EP | 2 062 540 | 4/2013 |
| EP | 2 481 356 | 9/2013 |
| EP | 2 642 954 | 10/2013 |
| EP | 2 451 361 | 11/2013 |
| EP | 2 688 630 | 1/2014 |
| EP | 2 311 380 | 4/2014 |
| EP | 2 744 423 | 6/2014 |
| EP | 2 531 113 | 12/2014 |
| EP | 2 116 190 | 9/2015 |
| EP | 2 043 527 | 10/2015 |
| EP | 2 967 867 | 1/2016 |

(56) References Cited

FOREIGN PATENT DOCUMENTS

| | | |
|---|---|---|
| EP | 2 623 039 | 7/2016 |
| EP | 3 069 661 | 9/2016 |
| EP | 1 469 790 | 10/2016 |
| EP | 2 398 395 | 5/2017 |
| EP | 2 757 962 | 6/2017 |
| EP | 2 108 315 | 9/2017 |
| EP | 2 819 585 | 11/2017 |
| EP | 3 054 855 | 11/2017 |
| EP | 3 253 297 | 12/2017 |
| EP | 3 297 541 | 3/2018 |
| EP | 2 688 486 | 5/2018 |
| EP | 3 329 860 | 6/2018 |
| EP | 2 004 068 | 8/2018 |
| EP | 3 367 917 | 9/2018 |
| EP | 2 753 246 | 11/2018 |
| EP | 3 398 533 | 11/2018 |
| EP | 3 398 537 | 11/2018 |
| EP | 2 259 728 | 3/2019 |
| EP | 3 071 118 | 8/2019 |
| EP | 3 151 753 | 9/2019 |
| EP | 2 207 500 | 10/2019 |
| EP | 2 744 412 | 10/2019 |
| EP | 3 146 937 | 10/2019 |
| EP | 2 952 157 | 1/2020 |
| EP | 1 827 247 | 4/2020 |
| EP | 2 999 412 | 5/2020 |
| EP | 2 422 709 | 6/2020 |
| EP | 2 757 957 | 11/2020 |
| EP | 2 416 736 | 12/2020 |
| EP | 3 122 284 | 1/2021 |
| EP | 2 731 510 | 4/2021 |
| EP | 2 741 679 | 10/2021 |
| FR | 2 305 165 | 10/1976 |
| FR | 2 714 284 | 3/1996 |
| FR | 2 827 153 | 1/2003 |
| GB | 2 407 985 | 5/2005 |
| WO | WO 1998/008462 | 3/1998 |
| WO | WO 2001/010306 | 2/2001 |
| WO | WO 2002/096295 | 12/2002 |
| WO | WO 2004/066811 | 8/2004 |
| WO | WO 2004/067092 | 8/2004 |
| WO | WO 2005/027752 | 3/2005 |
| WO | WO 2005/055834 | 6/2005 |
| WO | WO 2007/035726 | 3/2007 |
| WO | WO 2007/083288 | 7/2007 |
| WO | WO 2007/092274 | 8/2007 |
| WO | WO 2008/010738 | 1/2008 |
| WO | WO 2008/019590 | 2/2008 |
| WO | WO 2008/042229 | 4/2008 |
| WO | WO 2008/085235 | 7/2008 |
| WO | WO 2008/124603 | 10/2008 |
| WO | WO 2009/035610 | 3/2009 |
| WO | WO 2009/042866 | 4/2009 |
| WO | WO 2009/091425 | 7/2009 |
| WO | WO 2009/137755 | 11/2009 |
| WO | WO 2010/006061 | 1/2010 |
| WO | WO 2010/139771 | 12/2010 |
| WO | WO 2011/109792 | 9/2011 |
| WO | WO 2013/037005 | 3/2013 |
| WO | WO 2013/0175468 | 11/2013 |
| WO | WO 2015/059567 | 4/2015 |
| WO | WO 2016/087061 | 6/2016 |
| WO | WO 2016/192781 | 12/2016 |
| WO | WO 2017/136287 | 8/2017 |
| WO | WO 2018/085545 | 5/2018 |
| WO | WO 2018/166377 | 9/2018 |
| WO | WO 2018/213230 | 11/2018 |
| WO | WO 2020/225698 | 11/2020 |
| WO | WO 2020/247907 | 12/2020 |
| WO | WO 2021/050589 | 3/2021 |
| WO | WO 2021/146342 | 7/2021 |
| WO | WO 2022/091018 | 5/2022 |
| WO | WO 2022/091019 | 5/2022 |

* cited by examiner

INTERSEPTAL OCCLUDER DEVICE

FIELD OF THE INVENTION

In the most general aspect thereof, the present invention relates to an occluder device. In particular, the present invention relates to an interseptal occluder device. Even more in particular, the present invention relates to an interseptal occluder device of the type which can be re-crossed.

In particular, the present invention relates to a device for closing a defect of a septum or an opening obtained in a septum, not necessarily of the heart.

Even more in particular, the present invention relates to a device for closing a defect present in a septum, for example a defect in an atrial septum, so that the same defect, even if occluded, can subsequently be used for the crossing of a medical device through said defect.

Moreover, the device of the present invention is intended to occlude defects (typically congenital defects, but not only) or interatrial septum holes/openings created following percutaneous interventions with trans-septal puncture techniques (for example for mitral valve repair or left atrial appendage occlusion).

Still further, the present invention relates to devices and methods for closing defects such as a patent foramen ovale (PFO).

PRIOR ART

A septum is for example a thin wall which divides a cavity into two smaller cavities or chambers or compartments. The term "septum" is intended to define both a heart wall which divides two atria as well as a wall which divides the atrium and the right or left ventricle.

Referring to FIG. 1, an atrial septum 100 is a tissue wall which separates the right atrium 101 from the left atrium 102 of the heart 103.

A ventricular septum 104 is a tissue wall which separates the right 105 and left 106 ventricles of the heart 103.

A defect 107 of the septum 100, 104 can include a perforation or hole in the septum. A defect 107 of the septum 100, 104 can occur congenitally or by perforating the septum with a medical device to access a location inside the heart.

The femoral vein is an entry point for many catheterization laboratory procedures, with a smaller percentage of procedures using access to the arteries.

The atrial septum 100 is a percutaneous access point, for example for atrial fibrillation therapy, closure of the left atrial appendage, percutaneous repair of the mitral valve, and percutaneous replacement of the mitral valve. In these and other procedures, the devices must cross the atrial septum 100 and, in doing so, can leave an orifice in the atrial septum which cannot close or heal on its own.

Therefore, these defects are often closed using devices, such as clips or occluders. However, these devices do not allow re-crossing through the septum.

Therefore, there is a need for improved occlusion devices for closing a defect or opening the septum, and for re-crossing it in (possible) subsequent procedures.

Re-crossable occlusion devices are known from the prior art. These have an anchoring structure and a diaphragm or valve connected thereto.

For example, documents WO2017136287A1, US2014074155 and US2014012368A1 show re-crossable occluder solutions.

Document US20070073337 shows devices and methods for occluding the defects of internal tissues, such us septum defects, with clip-based devices. A device having a clip structure is shown, which includes a tubular body having at least a first and a second deflectable element coupled thereto. The first and second elements are coupled at the opposite ends of the tubular body and configured to switch from a non-deployed configuration to a deployed configuration. In the deployed configuration, each element extends outwards away from the tubular body in a position configured to rest on a tissue surface. The first and second elements of the clip are preferably configured to support a tissue wall therebetween and close any opening in the tissue wall. This solution does not allow re-crossing the device once implanted.

Document US20140012368 shows devices and methods for improving the implantation, retractability, or repositioning of a device for positioning a valve in a septum. The embodiments of the devices include pivotable sections which provide the ability to maintain the engagement of the device with a release system during implantation, in which the release system approaches an opening of the septum. The embodiments of the devices include configurations which allow for better recovery in a delivery system if a malfunction or problem with the patient's anatomy or physiology is detected. This device is used to implant a flow control valve. These solutions are devices for treating heart failure. In particular, it is intended to create interatrial pressure outlets, shunts, and the like, which reduce the high pressure on one side of the heart, thus mitigating the resulting symptoms. Therefore, this solution aims to create an opening in the septum. This flow control element is a tissue valve such as a tricuspid valve, a bicuspid valve or a single-leaflet valve formed by pericardial tissue from cattle, pigs, sheep or other animals, and therefore it has cusp-like foils made of preferably natural tissue and cusp-shaped.

Document US20160296684 shows endoluminal devices for treating heart failure, which include a central body adapted to allow the passage of interatrial blood, an anchor fixed to the central body adapted to keep the endoluminal device in place inside a defect present in the atrial septum of a patient's heart, and a control element rotationally engaged with the central body. The rotation of the control element in relation to the central body creates a bidirectional flow of interatrial blood which allows to reduce the high pressure in the right and left parts of the heart. This solution has a valve which, depending on the rotating position of a diaphragm, the position of which has been previously fastened, allows a blood flow. This valve is obtained with a central body shutter, the rigidity of which allows the central body to keep a certain radial force outwards, against the septum walls, thus reducing the risk of displacement or migration of the endoluminal device.

These solutions, although being advantageous in some aspects, are very complex to implement, and especially do not allow to substantially completely occlude the septum defect while freely choosing the crossing point or re-crossing point in different positions of the diaphragm, thus facilitating the approach of the surgical instrument to the surgery area which can be located very differently from patient to patient and from disease to disease.

Therefore, the need for an occlusion device which is simple to manufacture, easy to apply, and flexible to use after implantation for crossing the defect or the now-occluded opening of the septum in case of subsequent surgery is still strongly felt.

A PFO is a persistent, one-way, usually flap-like opening in the wall between the right atrium and the left atrium of the heart. Since left atrial pressure (LA) is normally higher than right atrial pressure (RA), the flap typically remains closed. Under certain conditions, however, the pressure of the RA can exceed the pressure of the LA, creating the possibility of a right-to-left shunt which can allow blood clots to enter the systemic circulation.

In a fetus, the foramen ovale serves as a physiological conduit for right-to-left shunting. After birth, with the establishment of pulmonary circulation, the increase in left atrial blood flow and pressure determine the functional closure of the foramen ovale. This closure is typically followed by the anatomical closure of the two overlapping layers of tissue, septum primum and septum secundum. However, a PFO has been shown to persist in a significant minority of adults.

The presence of a PFO has no therapeutic consequences in otherwise healthy adults, however, patients suffering from stroke or TIA in the presence of a PFO and without another cause of ischemic stroke are considered for prophylactic medical therapy to reduce the risk of a recurrent embolic event. These patients can be treated with oral anticoagulants, but such drugs can have negative side effects such as bleeding, bruising, and interactions with other drugs. In some cases, such as when the use of anticoagulant drugs is contraindicated, surgery may be used to suture a PFO closed. Suturing a PFO requires the attachment of the septum secundum to the septum primum with a stitch (continuous or interrupted), which is the common manner in which a surgeon closes the PFO under direct visualization.

The non-surgical closure of PFOs has become possible with umbrella devices and a variety of other similar mechanical closure models developed initially for the percutaneous closure of atrial septal defects (ASDs). These devices allow patients to avoid the potential side effects often associated with anticoagulant therapies. A solution is disclosed for example in US20050267524A1.

However, this known solution does not allow solving the aforementioned persistent problem of allowing re-crossing the occluded opening with a medical device where necessary subsequently, for example for the replacement of a mitral valve.

Document US2017224323 describes a method and device for closing a septum defect, or opening in the septum. In particular, it describes a method and a device for closing a septum defect, in particular an atrial septum defect, so that the septum defect can be accessed for reentry through the defect. This solution shows an annular structure forming a central opening through which a device is inserted through a valve structure. Therefore, this solution does not show any central structure with fastening element, and could not do it without compromising the functioning of the valve membrane (this solution shows only valve membranes).

Document US2014012368 relates to a valve structure as well. However, document US2014012368 discloses a PFO occluder. Although precisely for different applications, both of these two documents do not show an extended membrane above at least one of the anchoring branch roses (proximal or distal) of the supporting structure.

Therefore, the need remains strongly felt for an occluder device which allows to both repair defects in septa, but which at the same time allows the device to be re-crossed where it becomes necessary later.

SOLUTION

It is the object of the present invention to provide a re-crossable interseptal occluder device, having structural and functional features such as to meet the aforesaid needs and overcome the drawbacks mentioned above with reference to the devices of the prior art.

These and other objects are achieved by a device according to claim 1.

Some advantageous embodiments are the subject of the dependent claims.

DRAWINGS

Further features and advantages of the invention will become apparent from the description provided below of preferred exemplary embodiment thereof, given by way of non-limiting example, with reference to the accompanying drawings, in which:

FIGS. 25 and 26 show an axonometric and side view of an occluder device according to the invention and in which a membrane is connected to the arms or branches of a single end of the supporting structure;

DESCRIPTION OF SOME PREFERRED EMBODIMENTS

Figure 1:
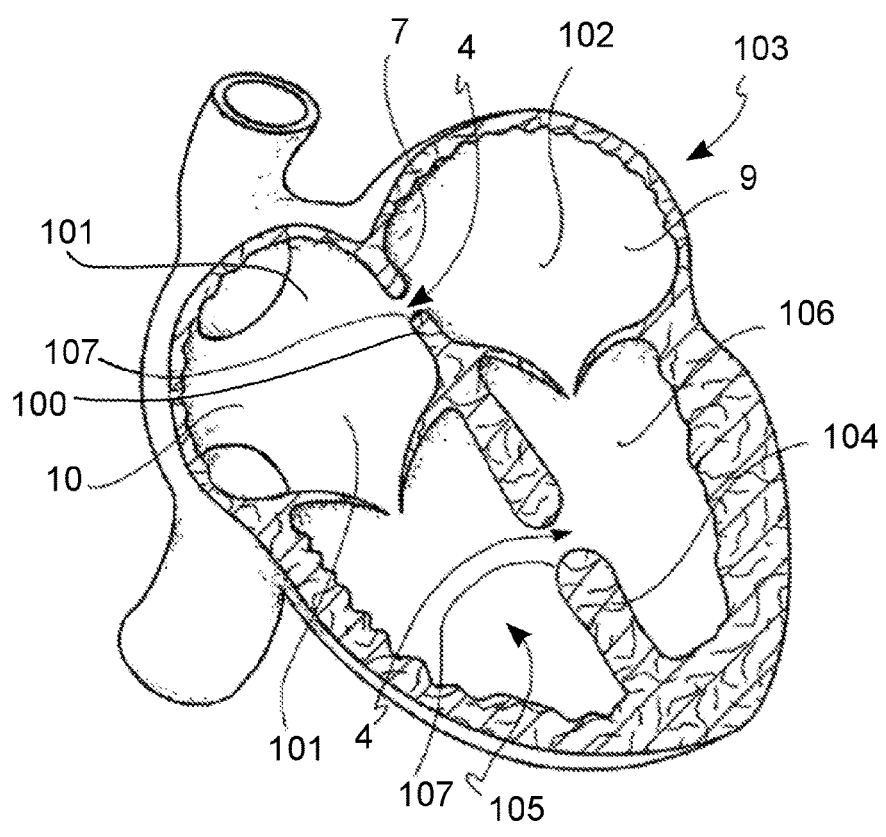
FIG. 1 depicts in section and diagrammatically a heart in which defects or openings are present in the atrial and ventricular septa.
Figure 2:
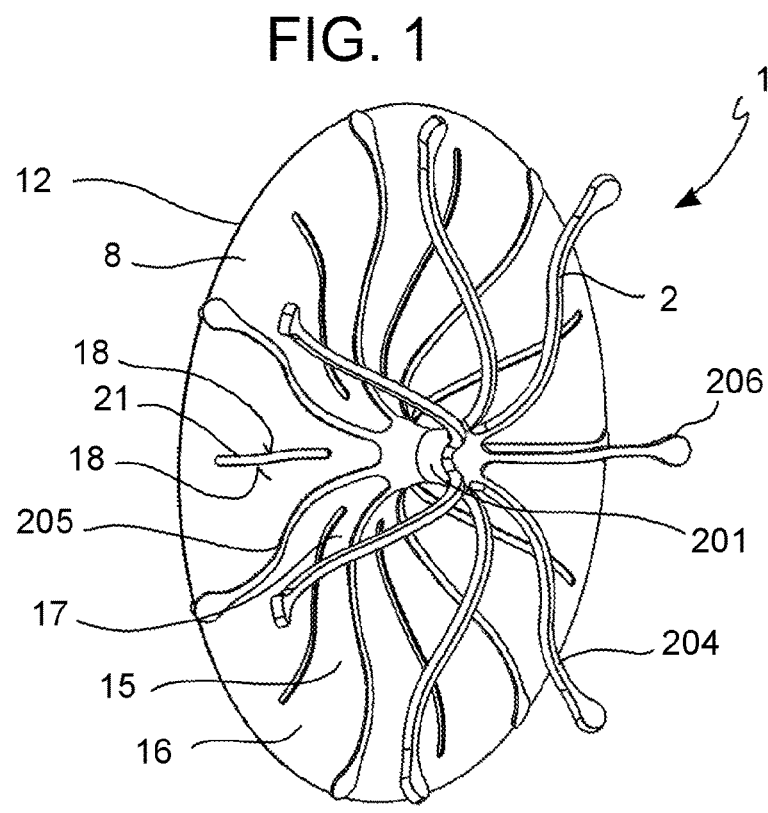
FIG. 2 shows an axonometric view of an occluder device according to a first embodiment of the present invention.
Figure 3:
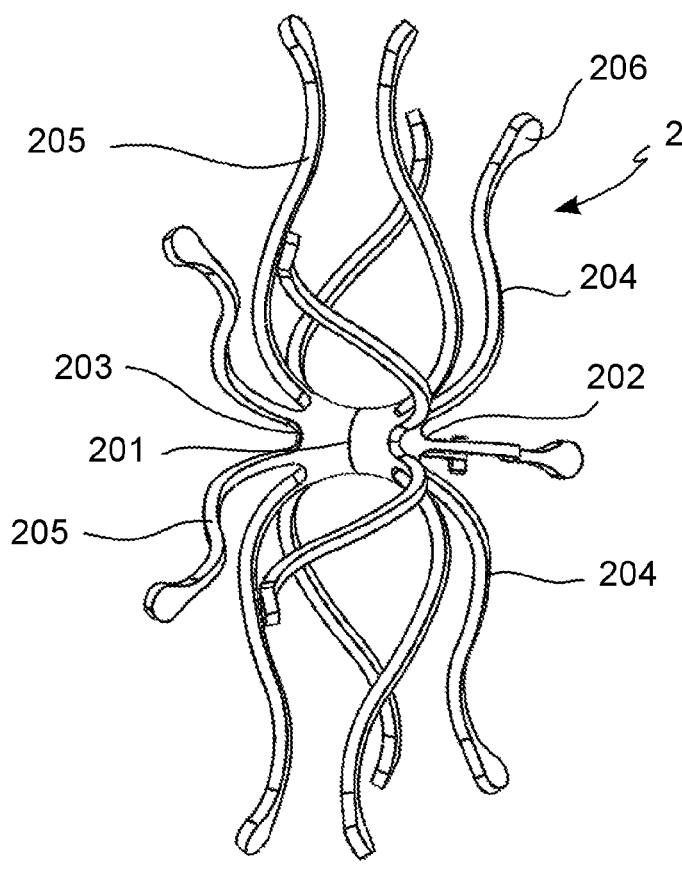
FIG. 3 shows an axonometric view of a supporting structure for an occluder device according to an embodiment of the solution of FIG. 2.
Figure 4:
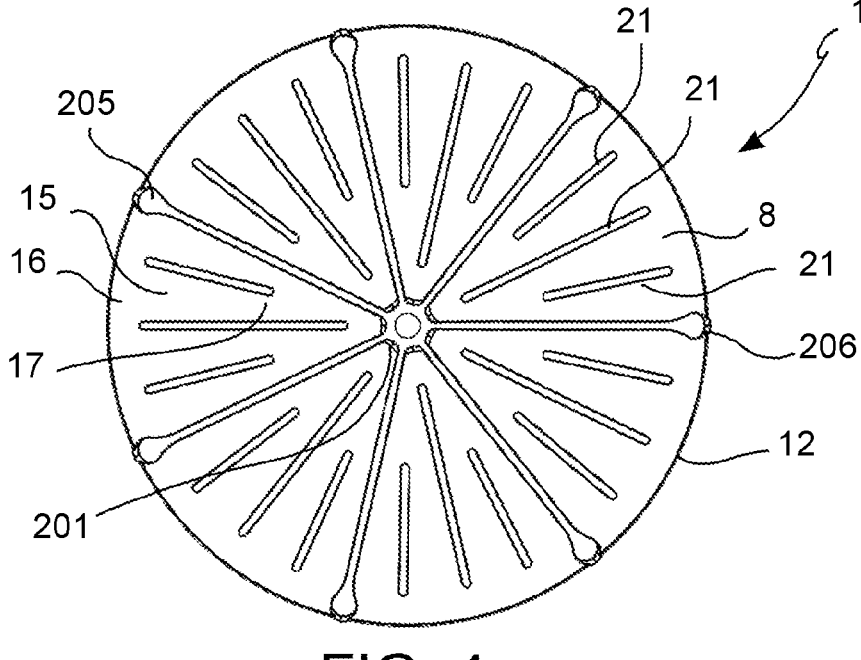
FIGS. 4 to 9 show in top view or in the direction of the axis X-X as many embodiments of an occluder device according to the present invention.
Figure 5:
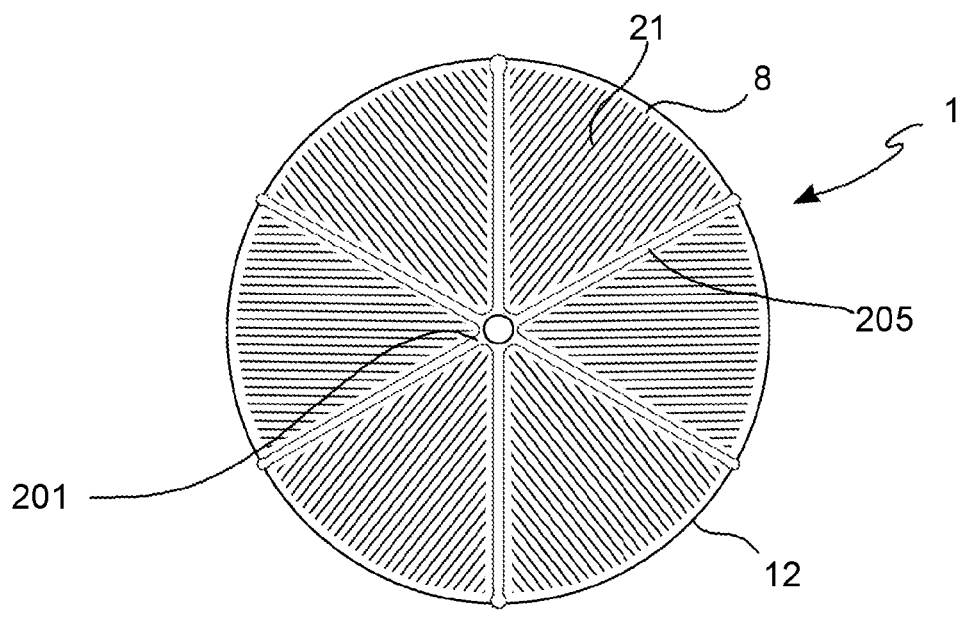
Figure 6:
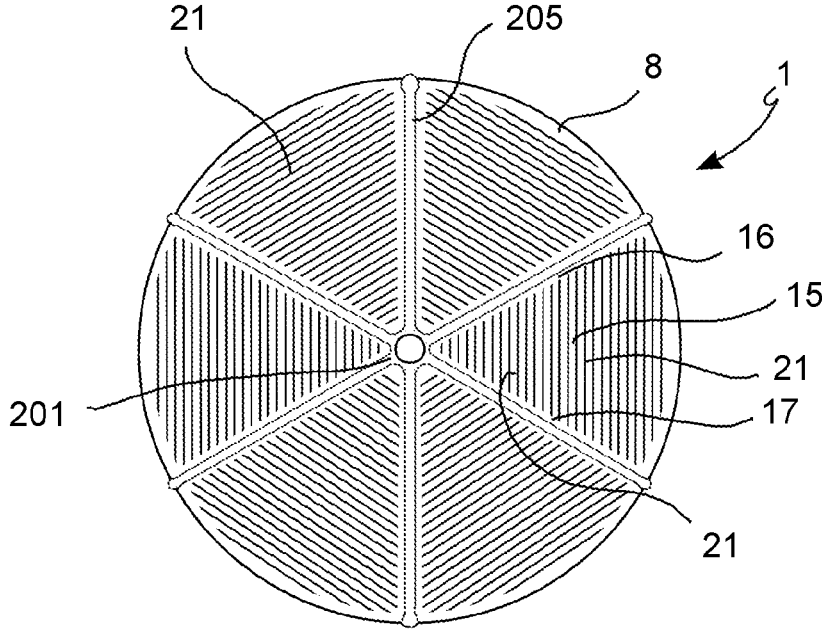
Figure 7:
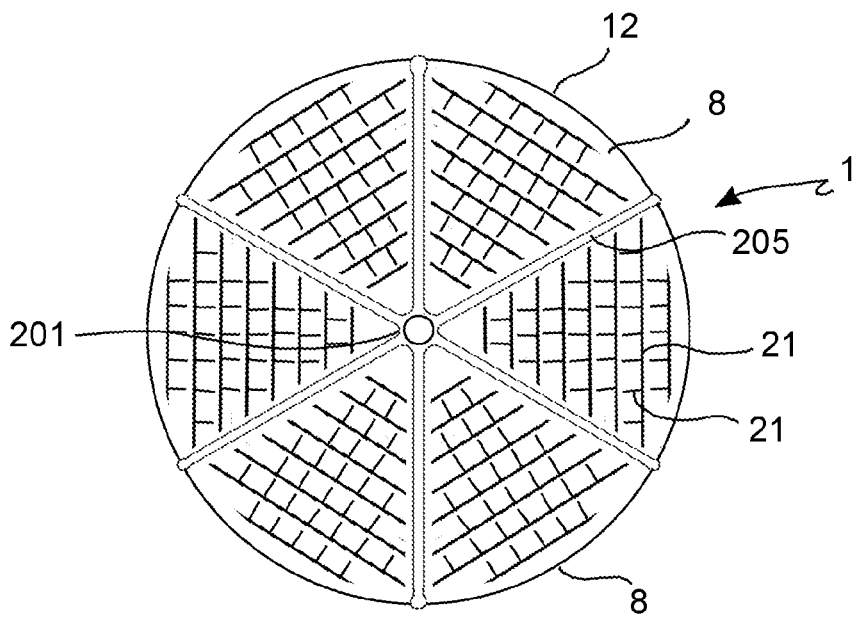
Figure 8:
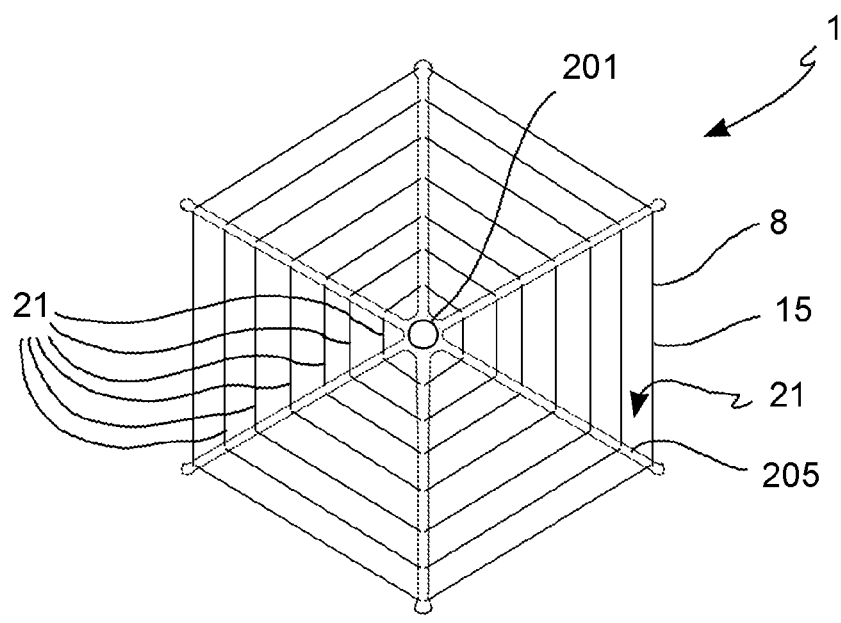
Figure 9:
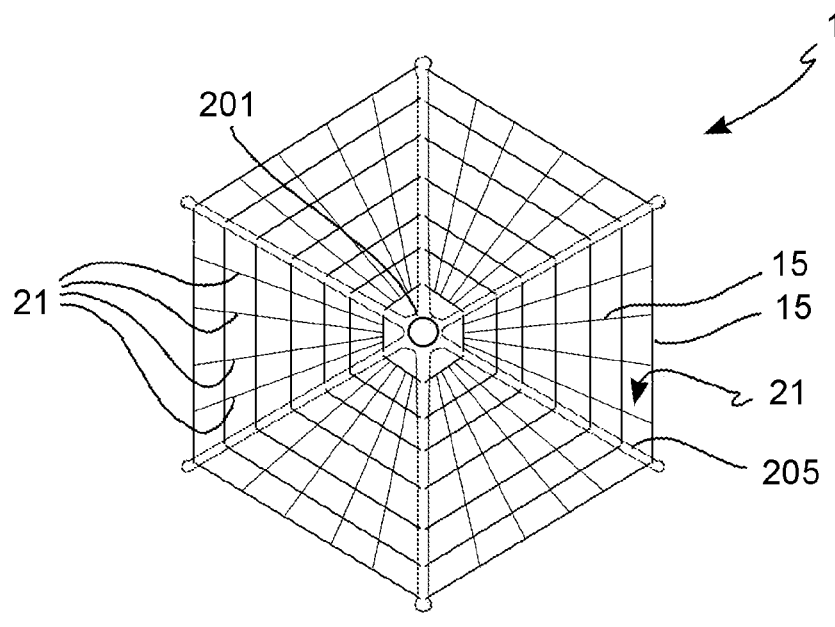
Figure 10:
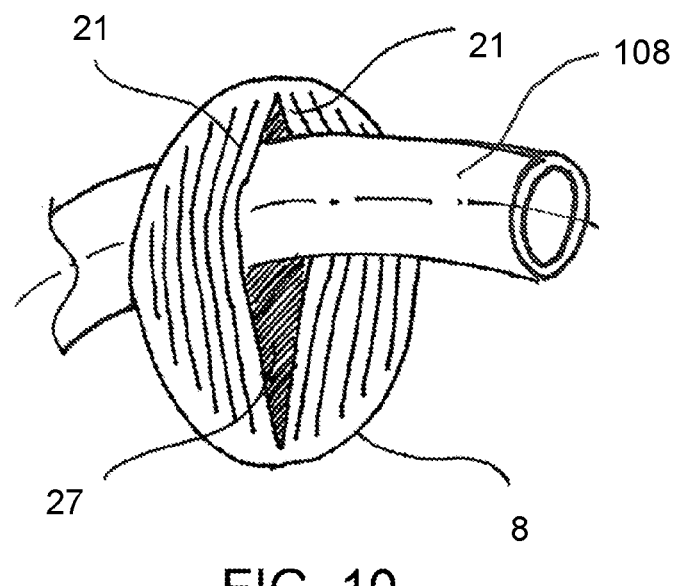
FIG. 10 shows an axonometric view of a detail of a membrane in a step of a crossing method by an external device.
Figure 11:
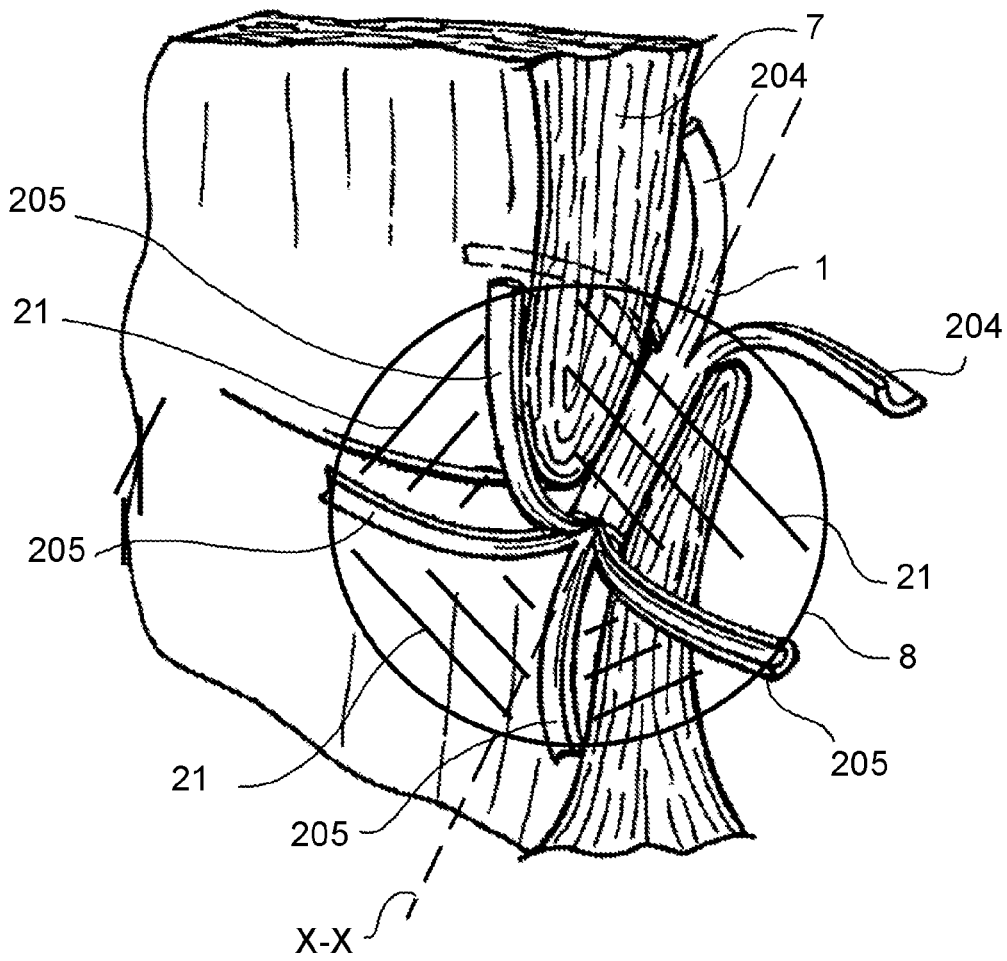
FIG. 11 shows a partially sectional view of an occluder device implanted in a PFO defect of a cardiac septum.
Figure 12:
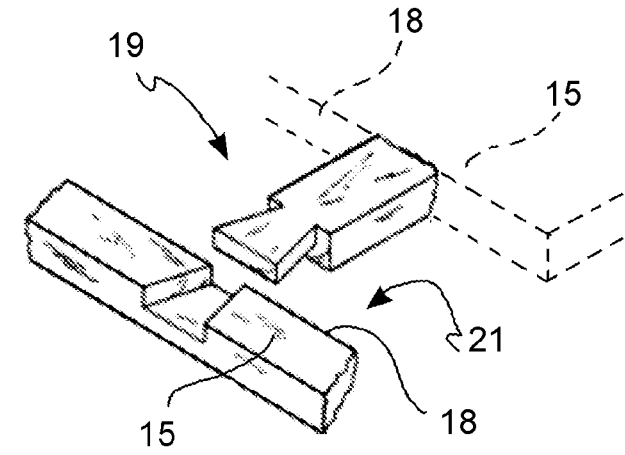
FIG. 12 shows a partially sectioned axonometric view of a detail of two facing slit edges temporarily connected to each other with a shape coupling.
Figure 13:
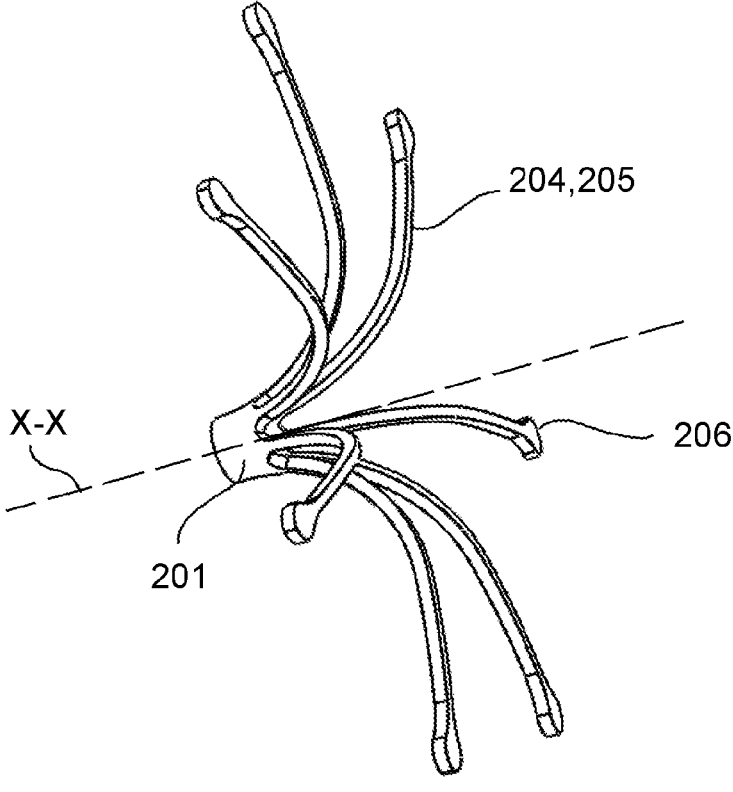
FIGS. 13, 14 and 15 show in axonometric view, according to the axis X-X and from the side, respectively, a portion of the supporting structure which is couplable to a similar or identical portion which is mirrored to form a supporting structure.
Figure 14:
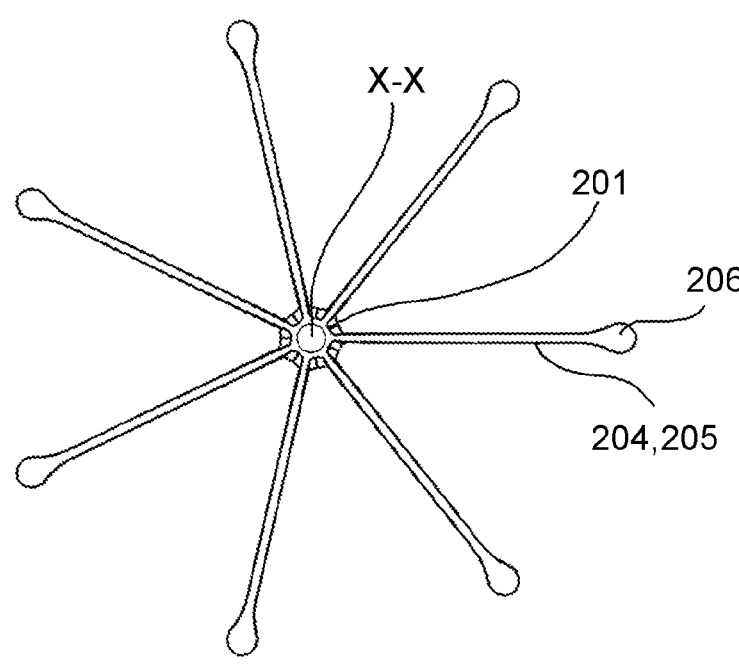
Figure 15:
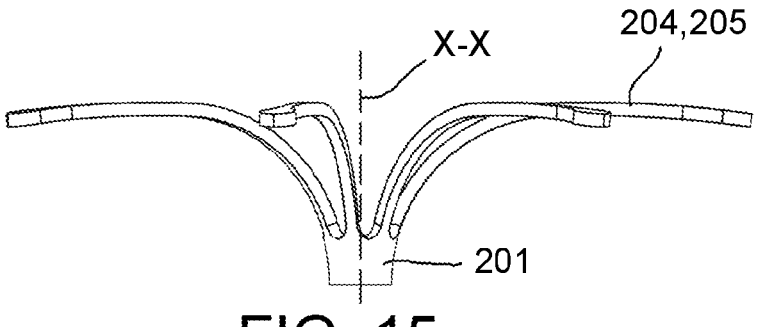
Figure 16:
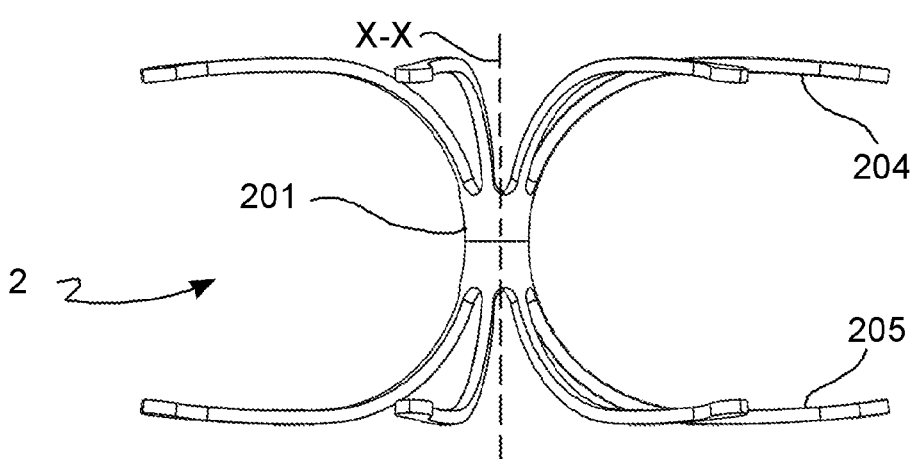
FIGS. 16 and 17 show a side view and according to the axis X-X, a supporting structure according to a further embodiment.
Figure 17:
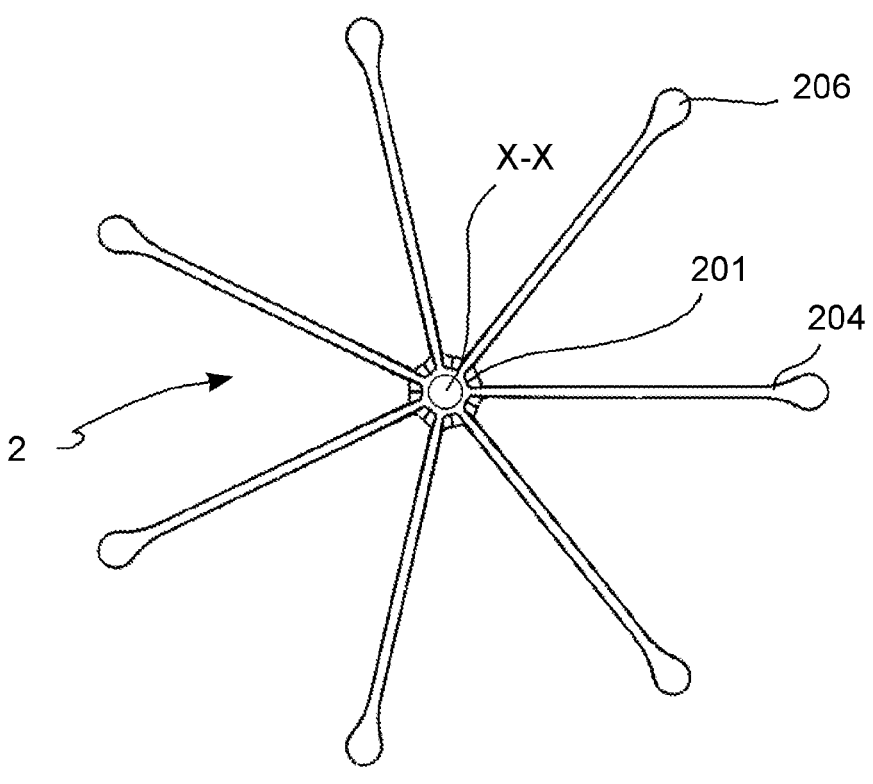
Figure 18:
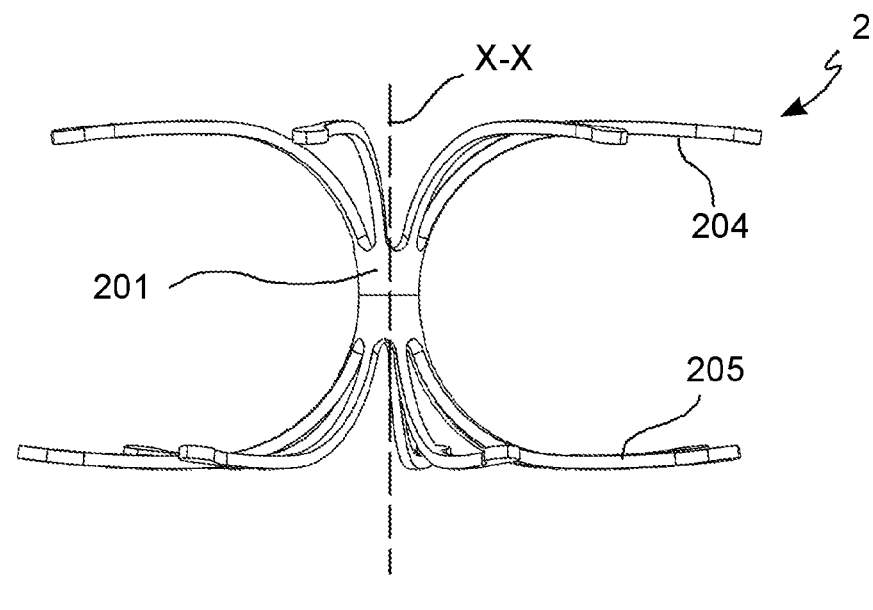
FIGS. 18 and 19 show a side view and according to the axis X-X, a supporting structure according to a further embodiment.
Figure 19:
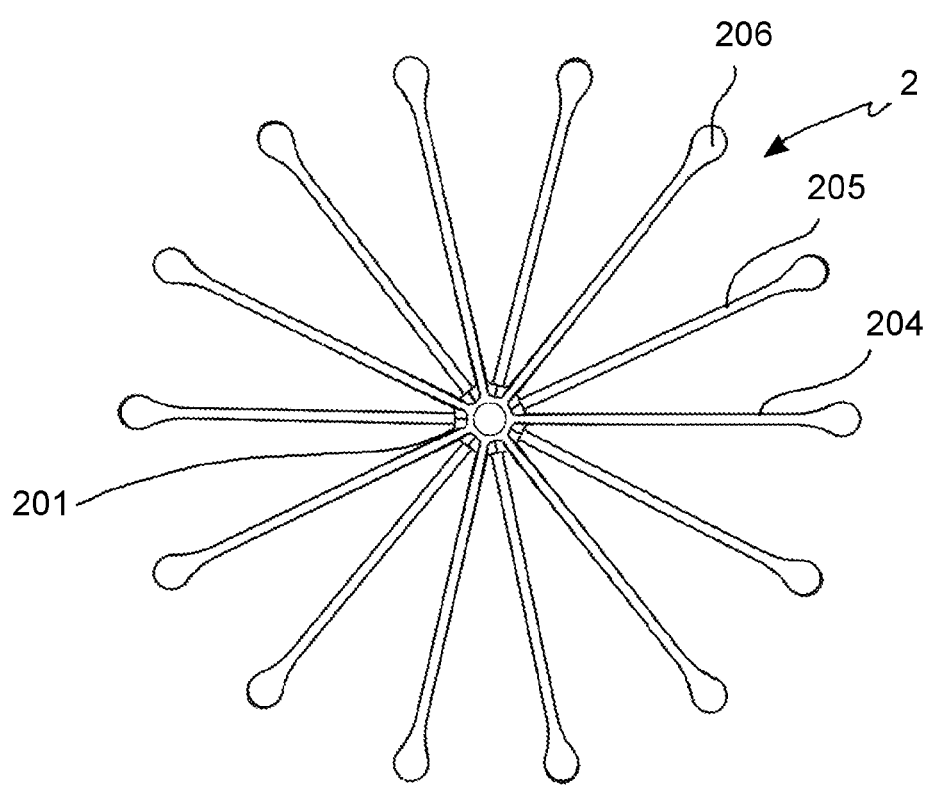
Figure 20:
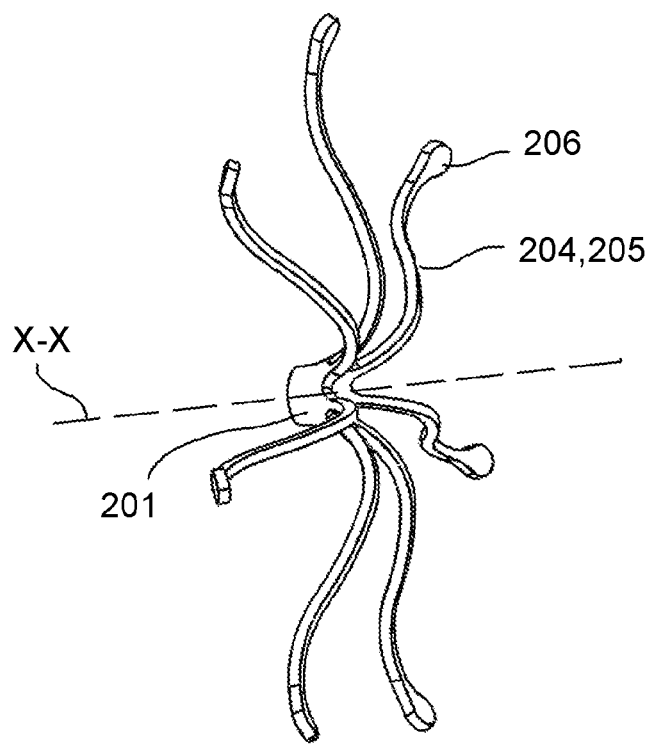
FIGS. 20, 21 and 22 show an axonometric view, a side view, and according to the axis X-X, a portion of a supporting structure according to a further embodiment.
Figure 21:
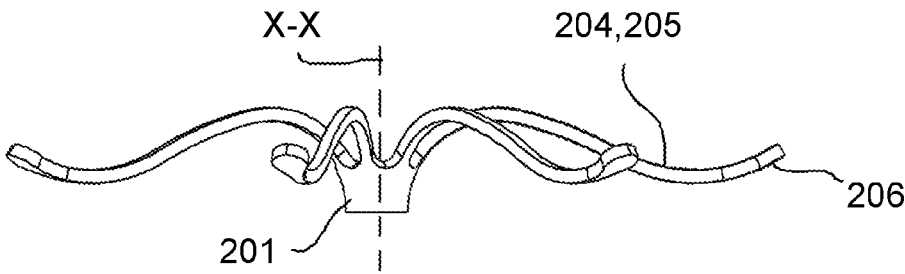
Figure 22:
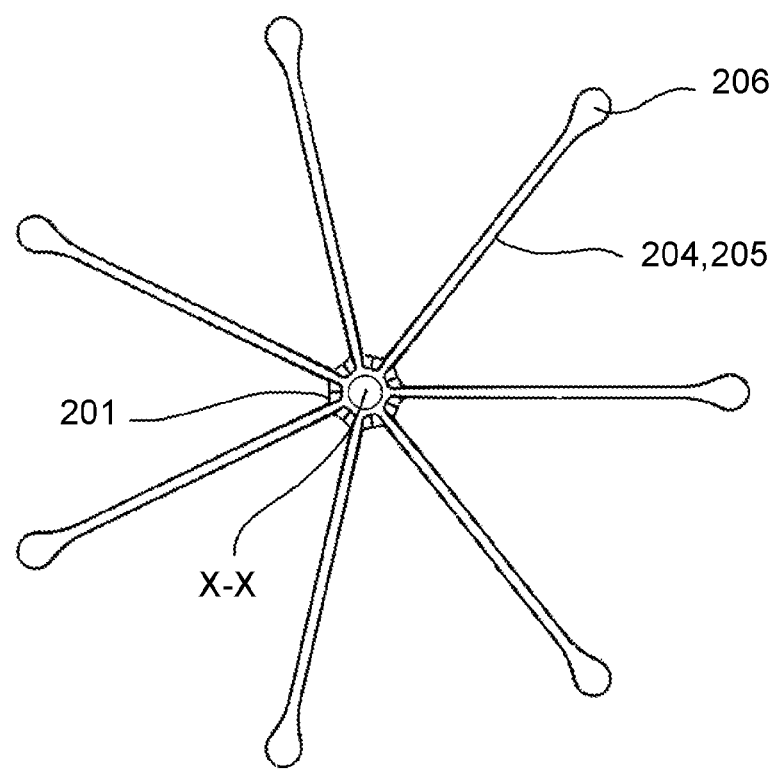
Figure 23:
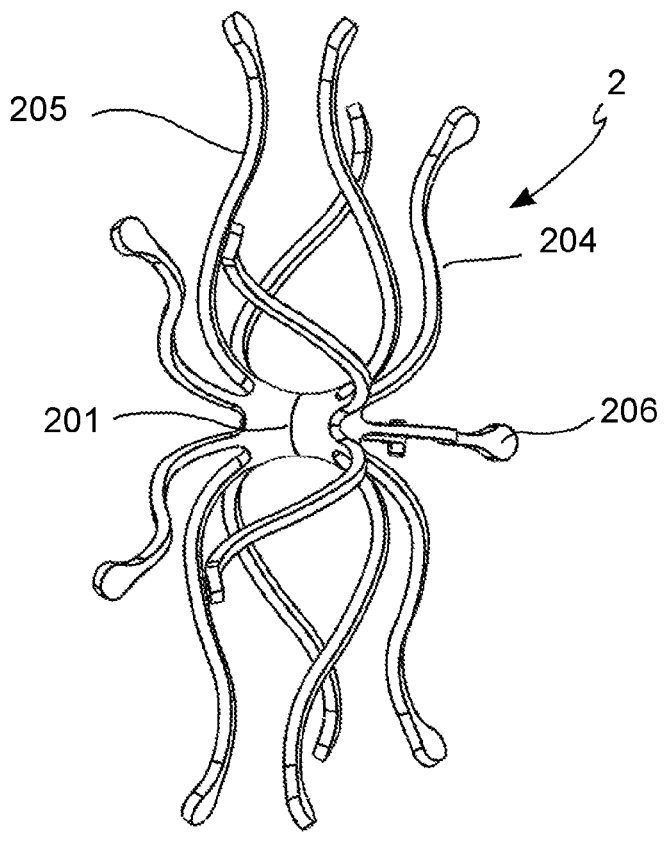
FIGS. 23 and 24 show an axonometric and side view, of a portion of a supporting structure according to a further embodiment.
Figure 24:
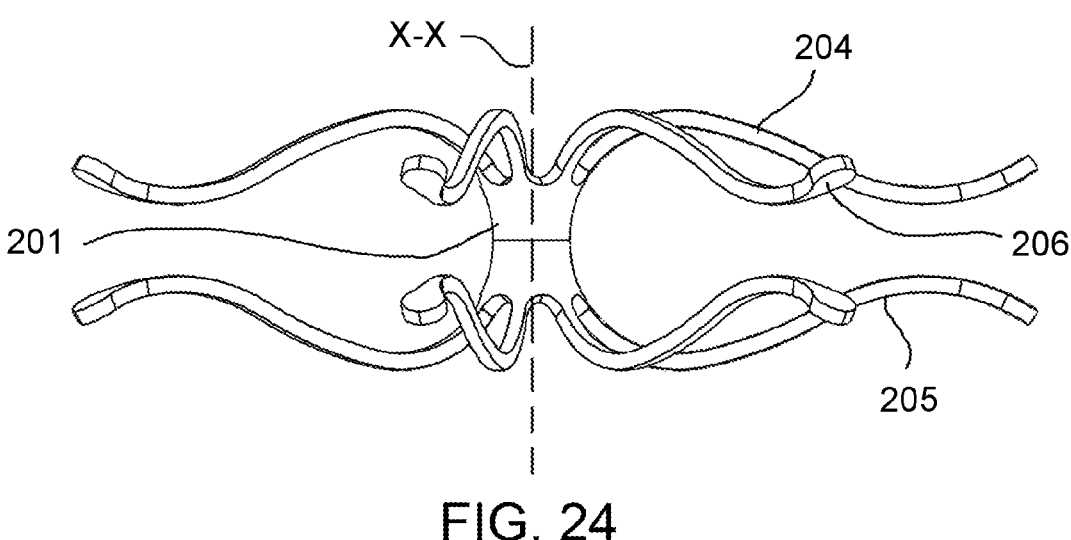
Figure 25:
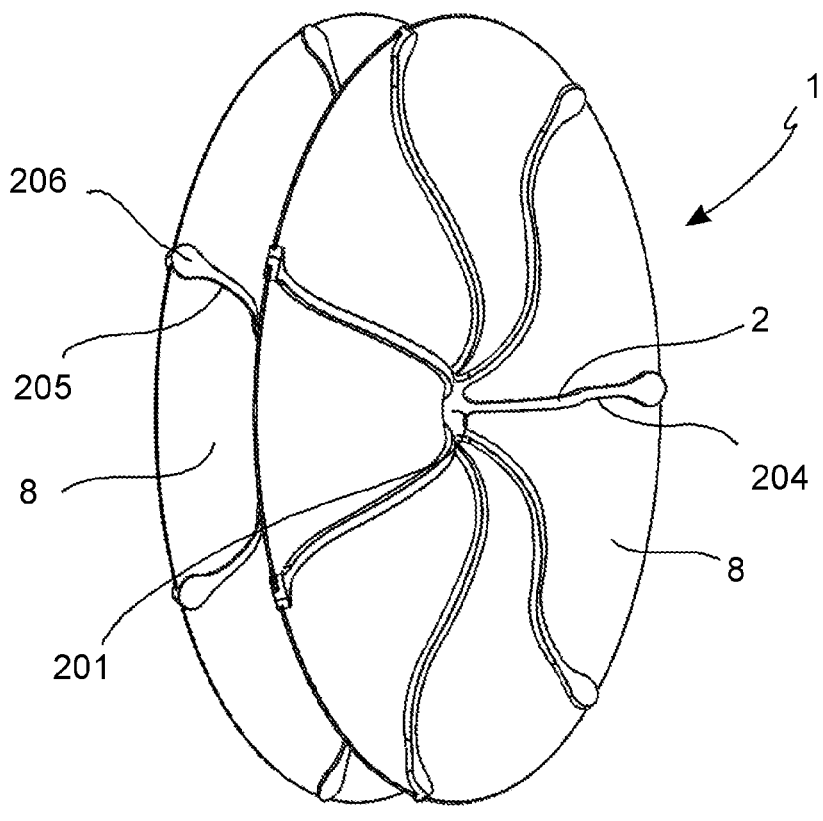
FIGS. 25 and 26 show an axonometric and side view of an occluder device according to the invention and in which a membrane is connected to the distal arms or branches and a membrane is connected to the proximal arms or branches.
Figure 26:
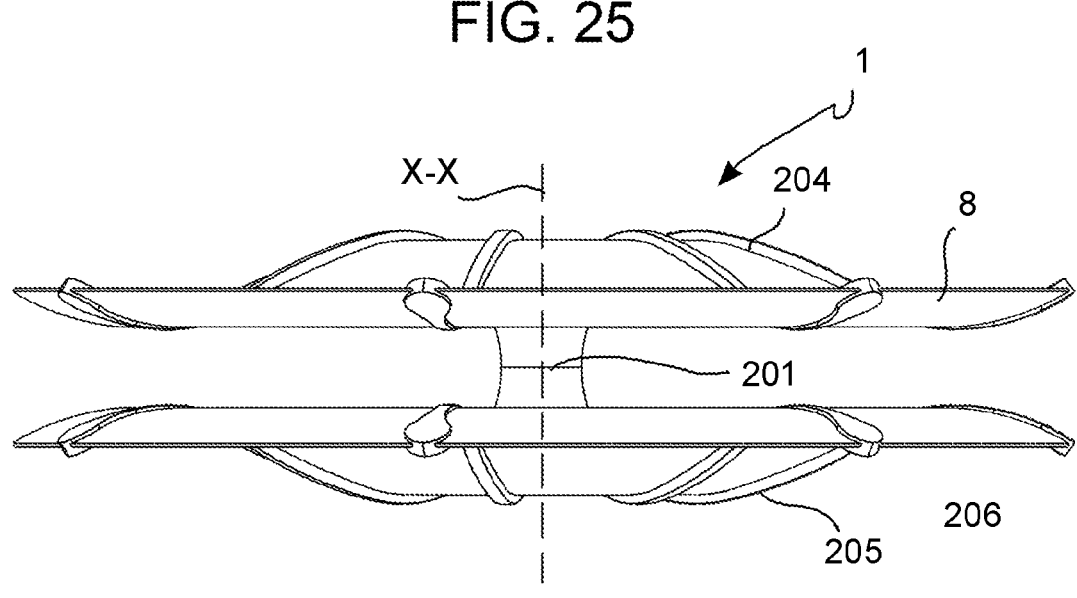
Figure 27:
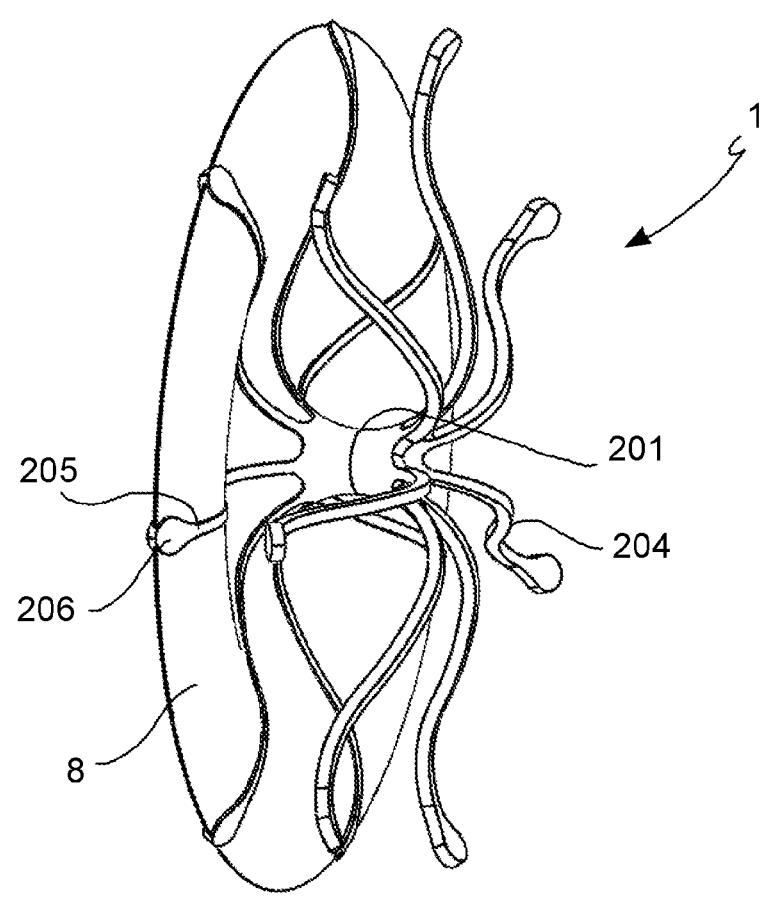
Figure 28:
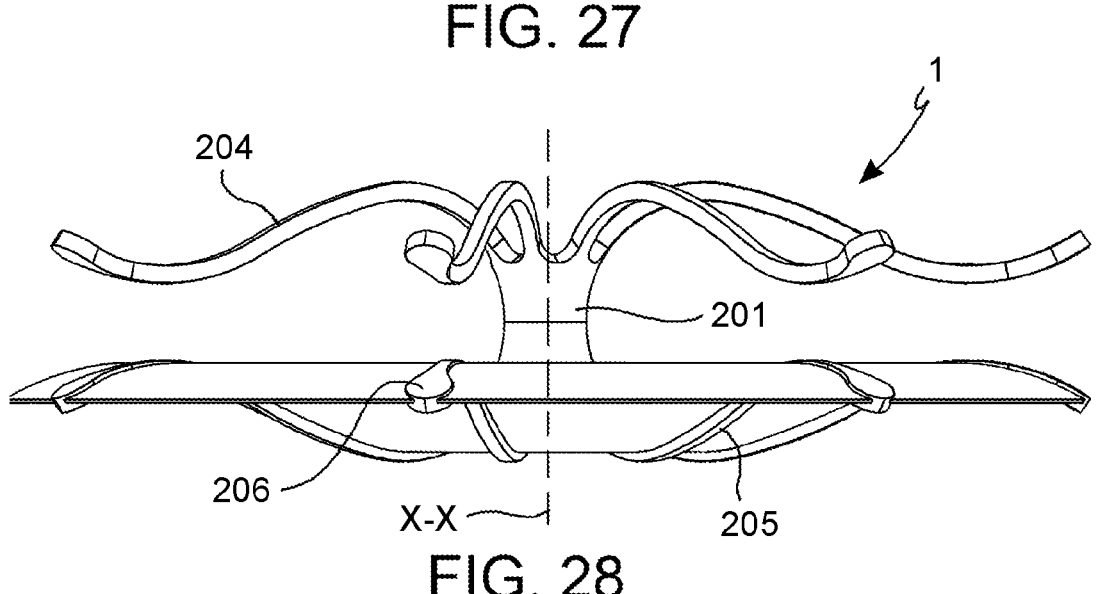
Figure 29:
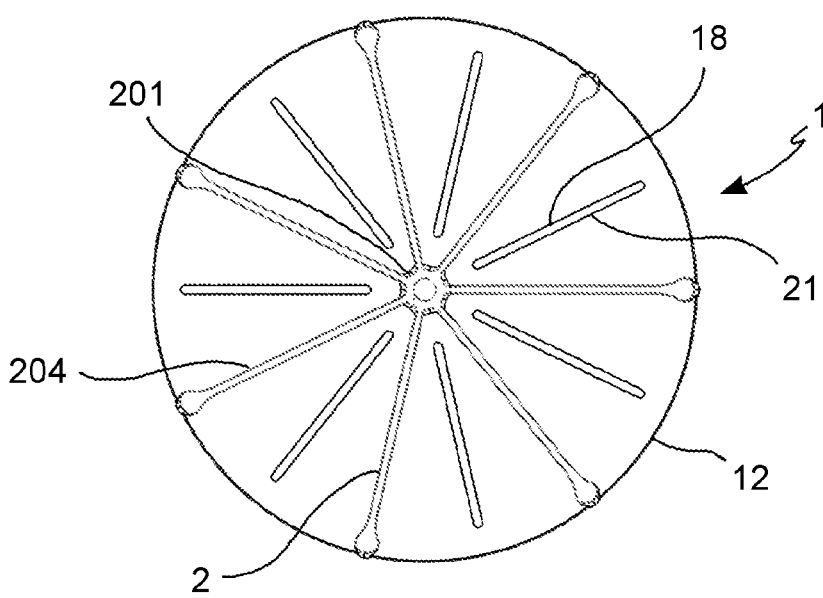
FIG. 29 depicts a view along the axis X-X of an occluder device according to the invention in which the slits have been highlighted.
Figure 30:
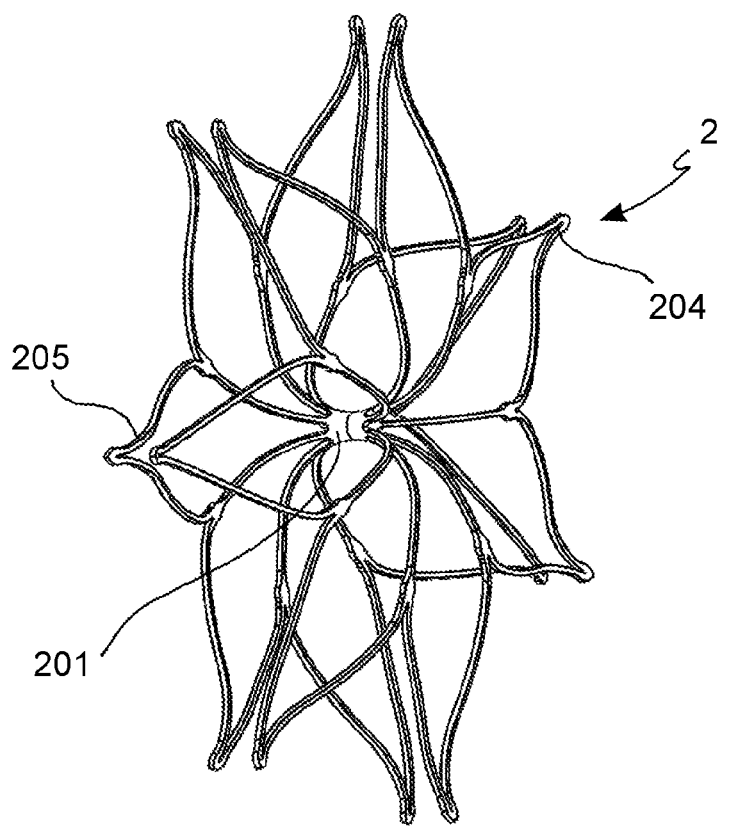
FIGS. 30, 31 and 32 show an axonometric view, a side view, and according to the axis X-X, a supporting structure according to a further embodiment.
Figures 31, 32:
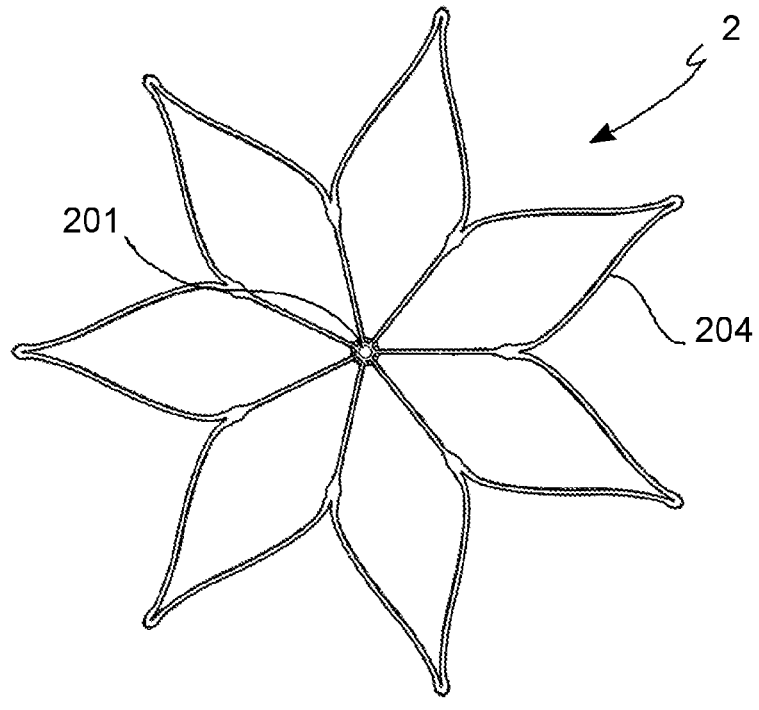
Figure 33:
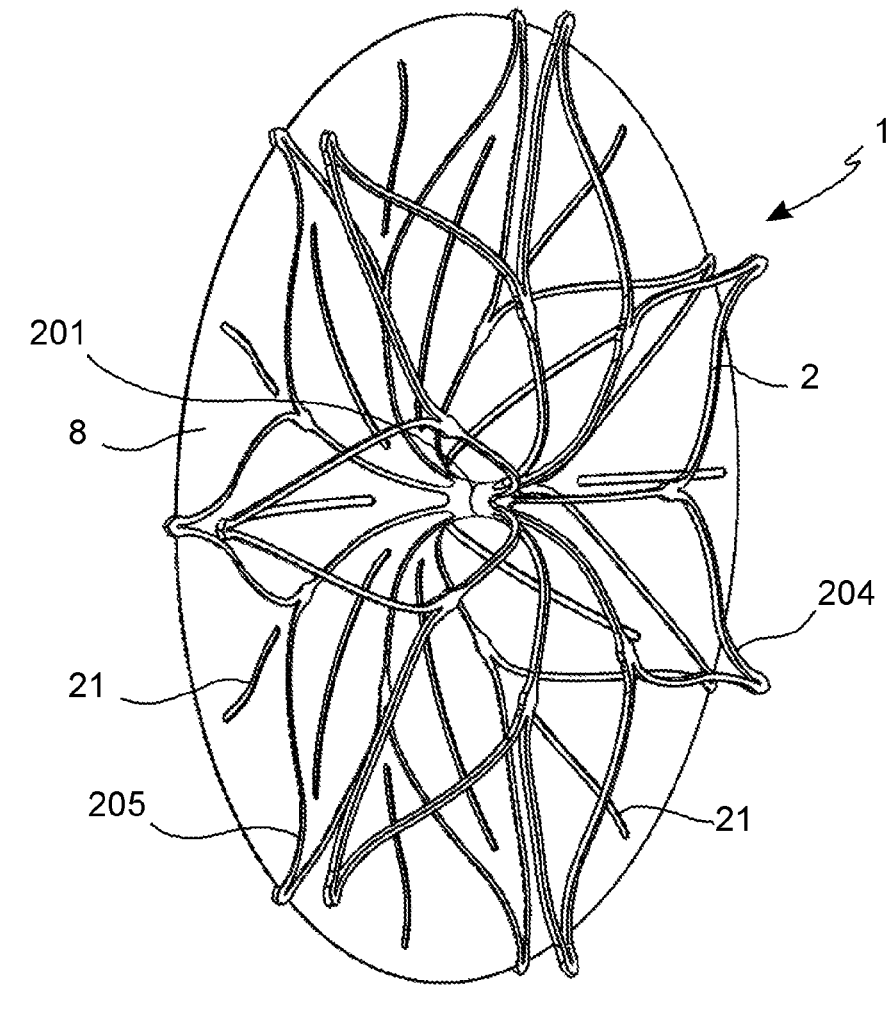
FIGS. 33, 34 and 35 show an axonometric view, a side view, and according to the axis X-X, an occluder device according to a further embodiment.
Figure 34:
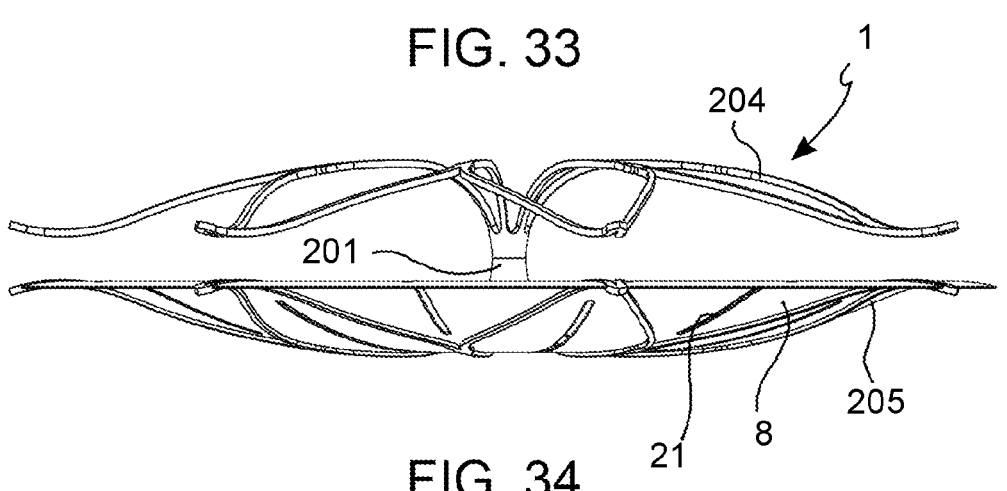
Figure 35:
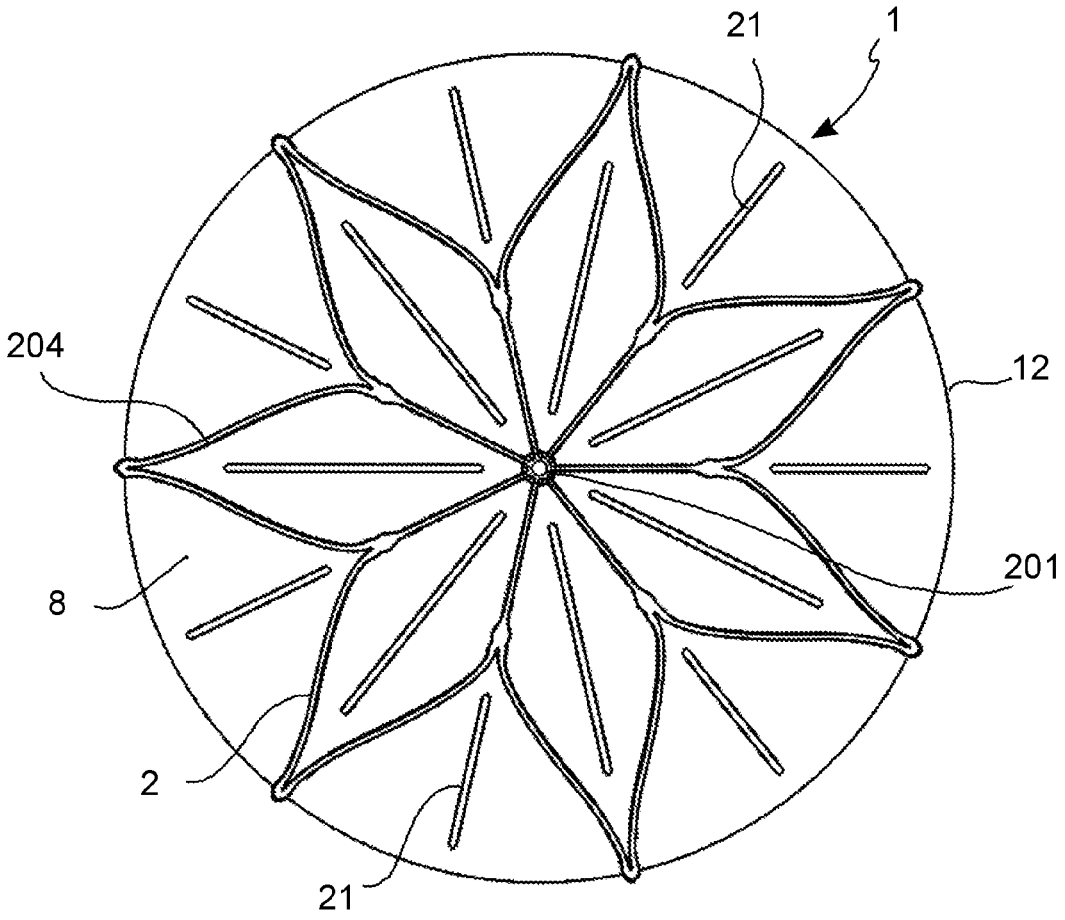
Figure 36:
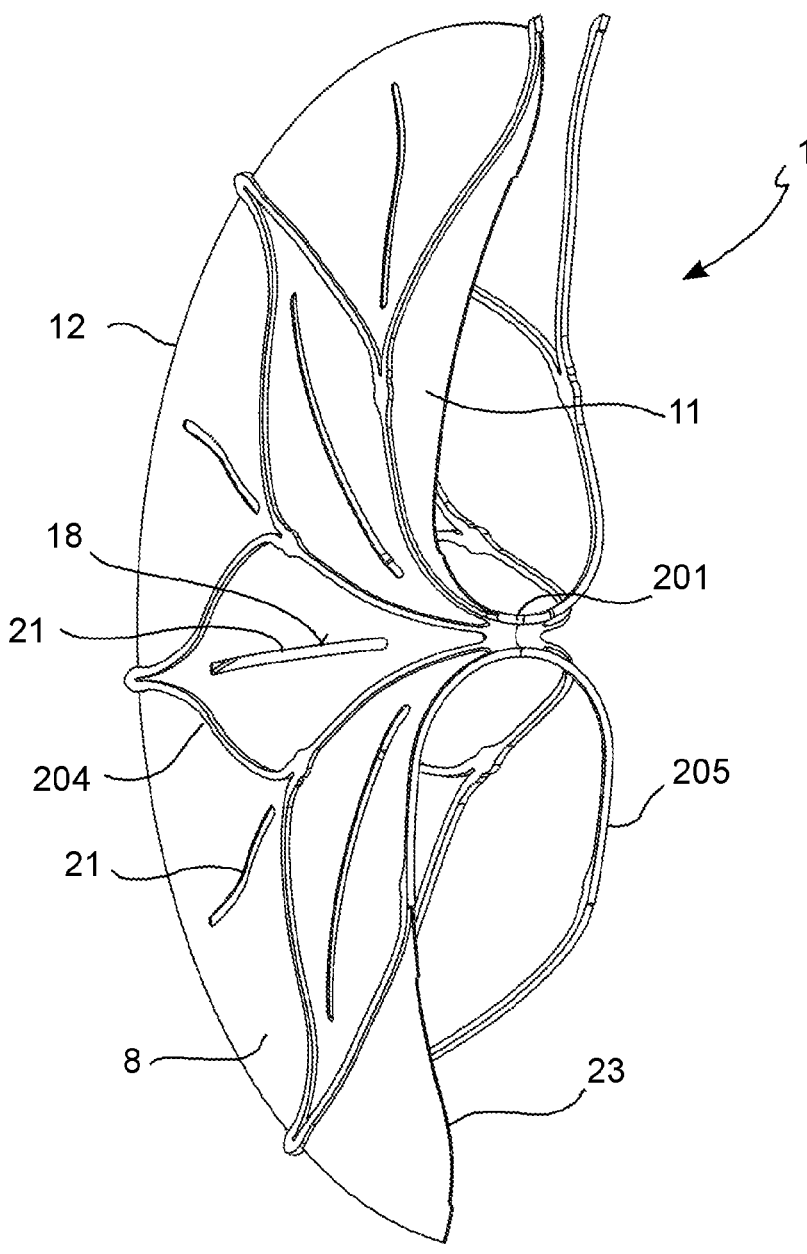
FIG. 36 shows an axonometric view of a cross-section passing through the axis X-X of the occluder device of FIG. 33.
Figure 37:
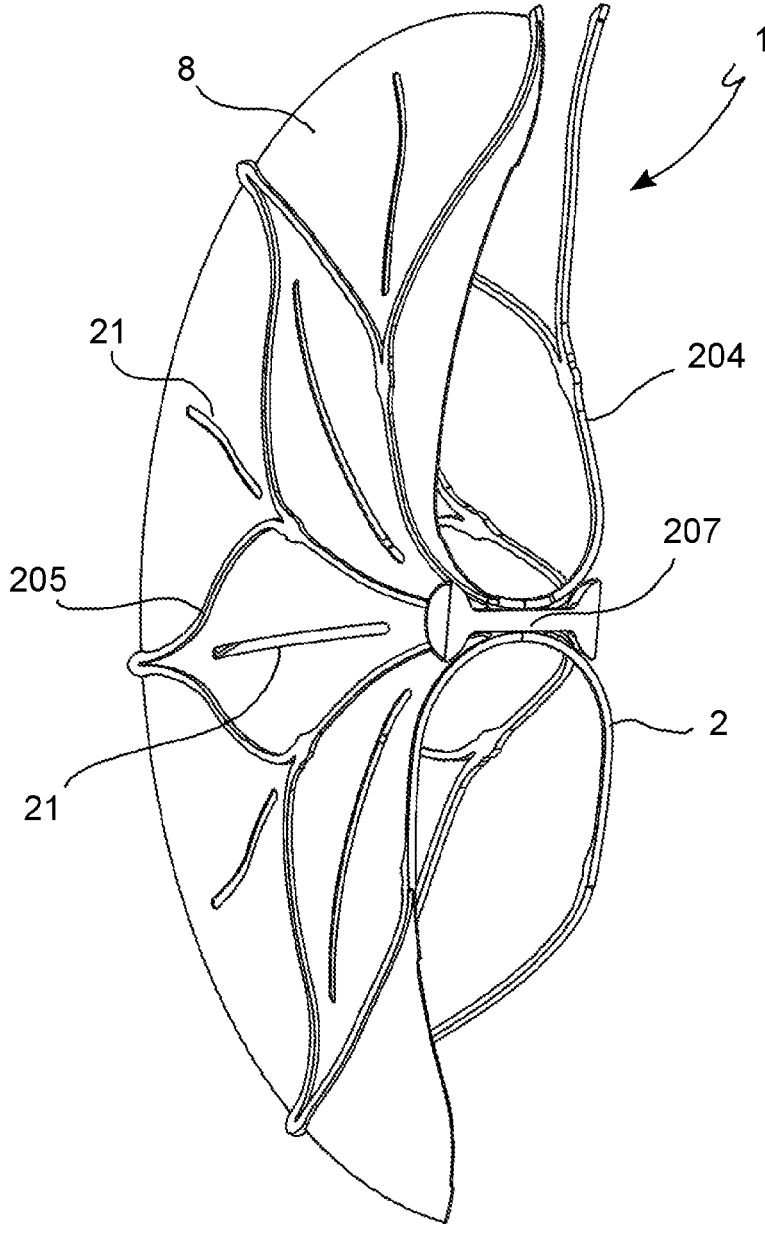
FIG. 37 shows an axonometric view of a cross-section passing through the axis X-X of an occluder device in which a stop element is included, according to a first embodiment, of the arms or branches in an unfolded position.
Figure 38:
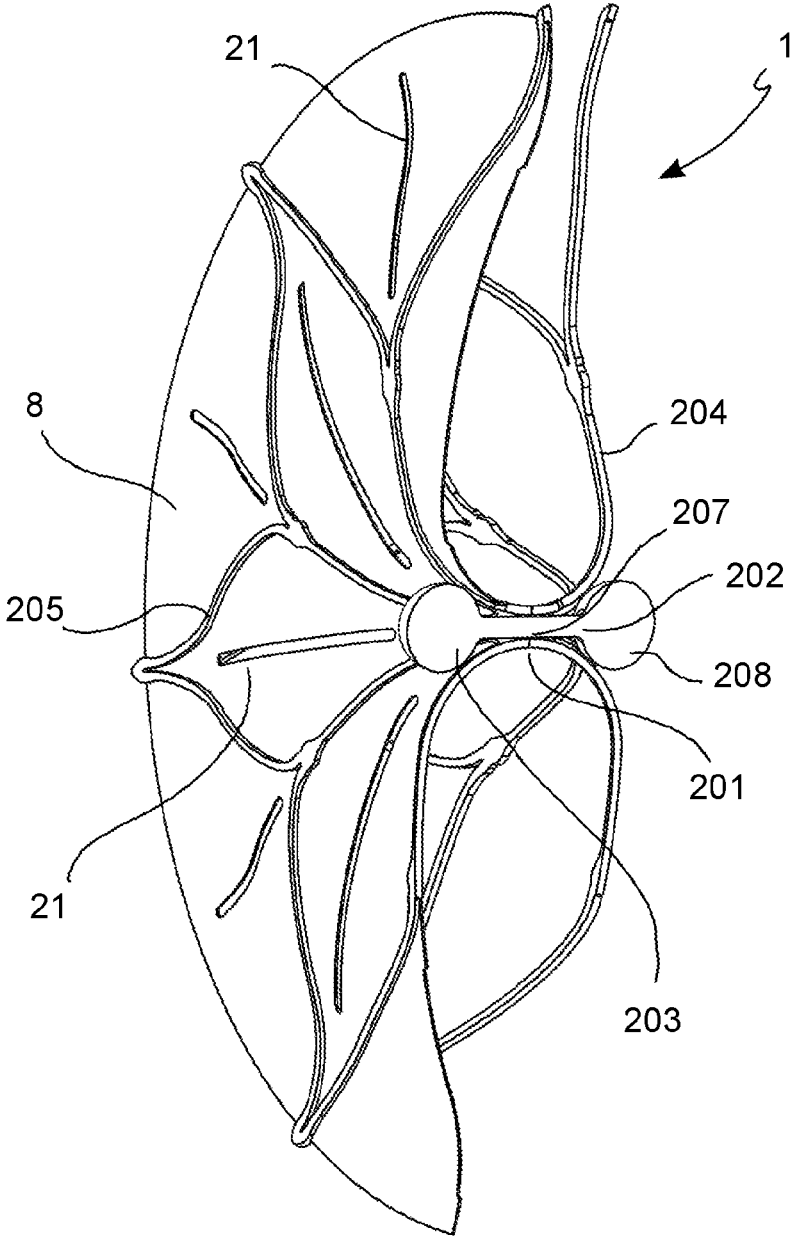
FIG. 38 shows an axonometric view of a cross-section passing through the axis X-X of an occluder device in which a stop element is included, according to a further embodiment, of the arms or branches in an unfolded position.
Figure 39:
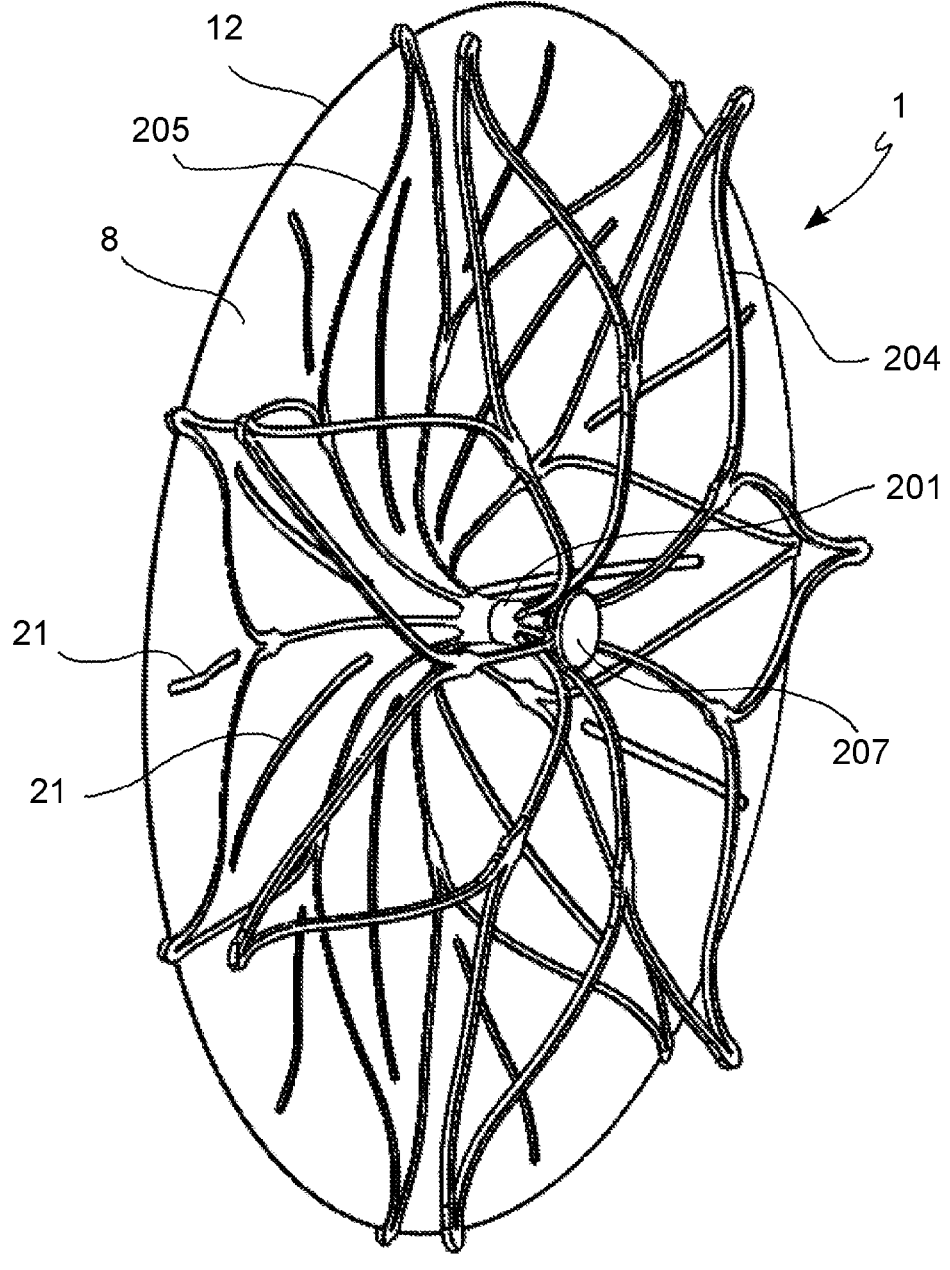
FIGS. 39, 40 and 41 show in two axonometric views and a side view an occluder device according to a further embodiment in which a stop element of the arms or branches is included in an unfolded position.
Figure 40:
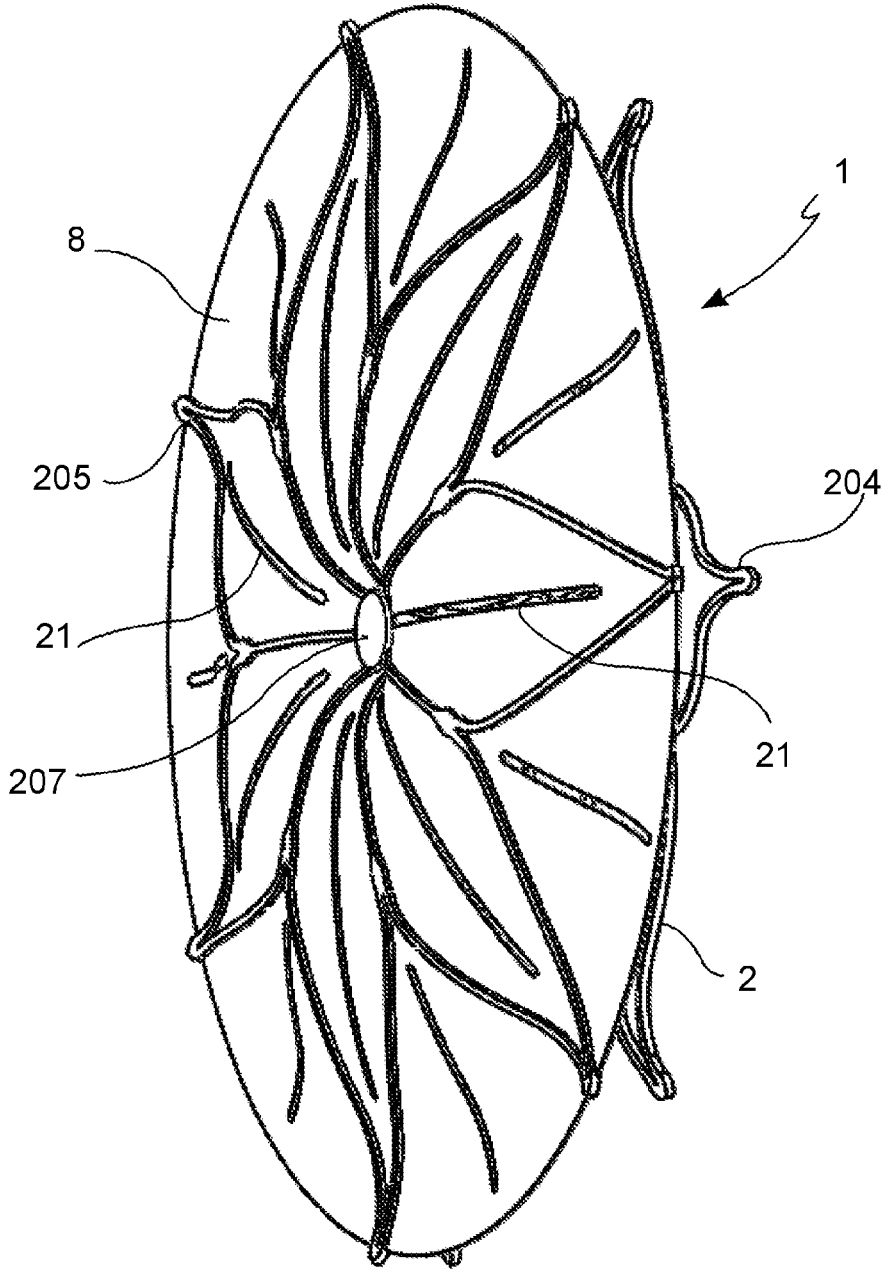
Figures 41, 42, 43, 44, 45:
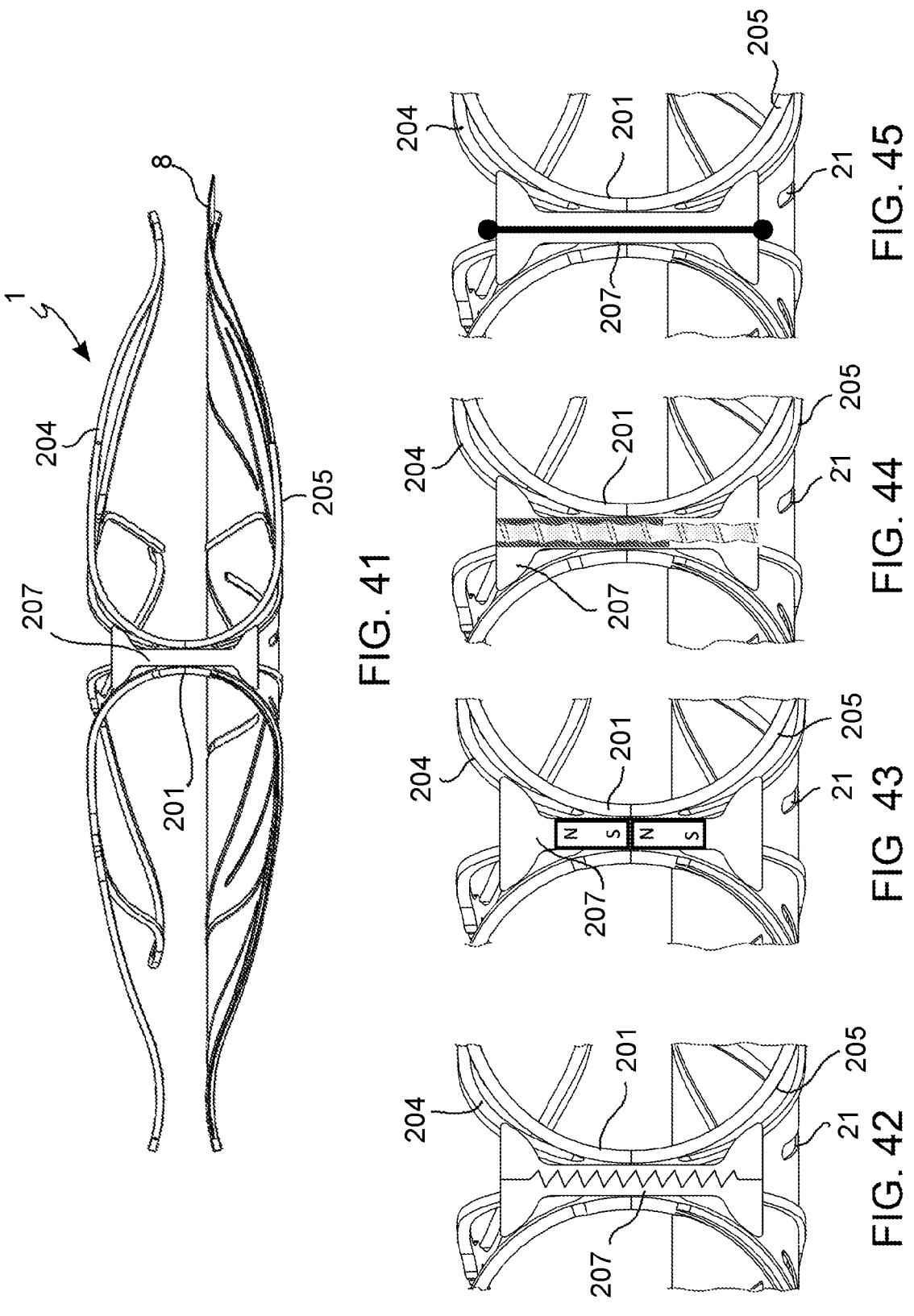
FIGS. 42, 43, 44 and 45 show in section a detail of the central portion of occluder devices in which different embodiments of the stop element of the arms or branches are included in an unfolded position.

In accordance with a general embodiment, an occlusion device 1 comprises, in accordance with a general embodiment, an occluder device 1 comprises a supporting structure 2.

Said supporting structure 2 comprises a central portion 201 having a distal end 202 and a proximal end 203.

Said supporting structure 2 comprises distal branches 204 extending away from said distal end 202 of the central portion 201.

Said supporting structure 2 comprising proximal branches 205 extending away from said proximal end 203 of the central portion 201.

Said proximal and distal branches 204, 205 define elastic hooked struts which are rotatable away from the central portion 201 to anchor a septum 7 of a heart 103.

Said occluder device 1 further comprising at least one membrane 8.

Said membrane 8 comprises a membrane body 11 connected to the distal or proximal branches 204; 205.

When the branches 204, 205 are in an unfolded or lying position, said membrane 8 has a closed position where the membrane 8 is in a configuration which provides maximum occlusion to the supporting structure 2.

Advantageously, the said membrane 8 comprises at least one slit 21, which, when actively engaged by an external device 108, the membrane 8 deforms the slit 21 which extends elastically, creating a passage lumen 27 for said external device 108.

In accordance with an alternative embodiment, said distal and proximal branches 204, 205 move from a folded position, where the distal and proximal branches 204, 205 are grouped near the central portion 201 or the virtual extension X-X thereof, to an unfolded, or lying, position, where the distal and proximal branches 204, 205 extend away from said central portion 201, and vice versa.

In accordance with an alternative embodiment, said distal and proximal branches 204, 205 are adapted to anchor the occluder device 1 to a septum 7 of a heart 103 when the supporting structure 2 crosses a septum defect 107 and said distal and proximal branches 204, 205 are in an open or lying position.

In accordance with an alternative embodiment, said central portion 201 is a tubular portion.

In accordance with an alternative embodiment, said central portion 201 defines a central axis X-X and said distal and proximal branches 204, 205 are arranged orthogonally with respect to the central axis X-X when the supporting structure 2 is in an unfolded or lying configuration and outside the human body.

In accordance with an alternative embodiment, said distal or proximal branches 204, 205 are equidistant from each other.

In accordance with an alternative embodiment, some of said distal or proximal branches 204, 205 have different lengths.

In accordance with an alternative embodiment, said distal or proximal branches 204, 205 are evenly distributed around a circumference.

In accordance with an alternative embodiment, said distal or proximal branches 204, 205 are unevenly distributed around a circumference.

In accordance with an alternative embodiment, each branch 205 extending from the proximal end 203 is aligned with a corresponding branch 204 extending from the distal end 202, when it is in position to lock an interposed tissue 7, 100, 104.

In accordance with an alternative embodiment, the proximal and distal ends 203, 202 each have branches 205, 204, in which each branch 205 extending from the proximal end 203 is offset at a circumferential angle of less than 180 degrees with respect to a corresponding branch 204 from the distal end 202.

In accordance with an alternative embodiment, said membrane has an external membrane periphery or membrane periphery 12.

Said at least one slit 21 extends from the membrane periphery 12 in a direction converging to said central portion 201.

In accordance with an alternative embodiment, said at least one slit 21 extends parallel to at least one branch 204, 205 of the supporting structure 2.

In accordance with an alternative embodiment, said at least one slit 21 extends along a circumferential path.

In accordance with an alternative embodiment, said at least one slit 21 extends along a path tangent to a circumference centered in said central portion 201.

In accordance with an alternative embodiment, said at least one slit 21 is a notch in the membrane body 1.

In accordance with an alternative embodiment, said at least one slit 21 are at least two slits 21.

In accordance with an alternative embodiment, said at least one slit 21 are a plurality of slits 21 uniformly distributed around said central portion 201.

In accordance with an alternative embodiment, said at least one slit 21 are at least two slits 21 and said at least two slits 21 extend parallel to each other.

In accordance with an alternative embodiment, said at least one slit 21 are at least two slits 21, said at least two slits 21 delimit a membrane portion forming a bridge 15 connecting two separate membrane portions 16, 17.

In accordance with an alternative embodiment, said separate membrane portions 16, 17 are arranged near branches 204, 205 facing each other.

In accordance with an alternative embodiment, said at least one slit 21 are cut edges or slotted edges 18 of the membrane 8.

In accordance with an alternative embodiment, said at least one slit 21 comprises slit edges 18; said slit edges 18 are shaped coupled, requiring force to separate, to keep the membrane 8 in a closed position during normal operation.

In accordance with an alternative embodiment, said at least one slit 21 comprises slit edges 18; said slit edges 18 are geometrically coupled like a jigsaw piece or dovetail joint 19.

In accordance with an alternative embodiment, the membrane 8, when actively engaged by an external device 108 elastically deforms to enlarge said at least one slit 21, forming said passage lumen 27.

In accordance with an alternative embodiment, said membrane comprises a membrane body 11, said membrane body 11 comprises a body structure which with the normal operation of the heart 103 remains in a closed position.

In accordance with an alternative embodiment, said at least one slit 21 is a slit which crosses the entire membrane 8 from a peripheral portion 16 of the membrane periphery 12 to a different peripheral portion 17 of the membrane periphery 12.

In accordance with an alternative embodiment, said membrane 8 has a circular shape and said at least one slit 21 is a slit which crosses the entire membrane 8.

In accordance with an alternative embodiment, said membrane 8 is a wire.

In accordance with an alternative embodiment, said membrane is a plurality of wires.

In accordance with an alternative embodiment, said membrane is a plurality of interconnected wires.

In accordance with an alternative embodiment, said membrane comprises a membrane body 11, the membrane body 11 has a membrane thickness 23.

Said membrane thickness 23 increases towards the membrane periphery 12 of the membrane 8.

In accordance with an alternative embodiment, said membrane comprises a membrane body 11, said membrane body 11 comprises at least one rib 29.

In accordance with an alternative embodiment, said membrane body 11 comprises at least one rib 29; said at least one rib 29 is arranged radially.

In accordance with an alternative embodiment, said membrane body 11 comprises at least one rib 29; said at least one rib 29 is arranged circumferentially.

In accordance with an alternative embodiment, said membrane 8 comprises magnets 31.

In accordance with an alternative embodiment, said membrane 8 comprises magnets 31, said magnets 31 are embedded in the membrane body 11 to keep the membrane 8 in a closed position during normal operation.

In accordance with an alternative embodiment, said membrane 8 comprises magnets 31, said magnets are embedded in the slit edges 18 to keep the membrane 8 in a closed position during normal operation.

In accordance with an alternative embodiment, said occluder device 1 comprises two membranes 8, in which said two membranes 8 are overlapped.

In accordance with an alternative embodiment, said occluder device 1 comprises two membranes 8, in which said two membranes 8 are overlapped and supported at the same branches 204, 205.

In accordance with an alternative embodiment, said occluder device 1 comprises two membranes 8, in which said two membranes 8 are overlapped and the at least one slit 21 of a first membrane 8 avoids completely overlapping the at least one slit 21 of the second membrane 8.

In accordance with an alternative embodiment, said occluder device 1 comprises two membranes 8, in which said two membranes 8 are overlapped and the at least one slit

21 of a first membrane 8 extends along a first slit path, and the at least one slit 21 of a second membrane 8 extends along a second slit path.

Said first slit path crosses said second slit path;

In accordance with an alternative embodiment, said occluder device 1 comprises two membranes 8, in which said two membranes 8 are overlapped and the at least one slit 21 of a first membrane 8 extends along a first slit path, and the at least one slit 8 of a second membrane extends along a second slit path.

Said first slit path crosses said second slit path in a region in which the first and second slit paths are orthogonal, when observing the membrane 8 from a transverse direction to said slit paths.

In accordance with an alternative embodiment, said occlusion device 1 is a structure the purpose of which is to occlude a lumen 4, 107 to prevent the flow through said lumen 4, 107.

In accordance with an alternative embodiment, said supporting structure 2 is a structure which provides the attachment to the anatomy of the heart 103, for example the tissue of a septum 7, 100, 104.

In accordance with an alternative embodiment, said membrane 8 is an elastically flexible occlusive sheet.

In accordance with an alternative embodiment, said membrane 8 is a flexible occlusive sheet with a much lower thickness 23 than the height and width thereof.

In accordance with an alternative embodiment, said closed position is the passive configuration of the membrane 8 in which said membrane 8 occludes the maximum cross-sectional area of which it is capable.

In accordance with an alternative embodiment, said membrane periphery 12 of the membrane is the outer margin of the membrane 8.

In accordance with an alternative embodiment, said slit 21 is an unsupported edge of the membrane 8.

In accordance with an alternative embodiment, said slit 21 is an unsupported edge of the membrane 8, or slit edge 18, said slit edge 18 is linear.

In accordance with an alternative embodiment, said slit 21 is an unsupported edge of the membrane 8, or slit edge 18, said slit edge 18 is curved.

In accordance with an alternative embodiment, said external device 108 is a medical device actively brought into apposition with the membrane 8, i.e., for example a catheter.

In accordance with an alternative embodiment, said passage lumen 27 is a lumen inside the membrane 8 large enough to allow the passage of an external device 108.

In accordance with an alternative embodiment, said supporting structure 2 is obtained from a tubular structure.

In accordance with an alternative embodiment, said supporting structure 2 is obtained from a tubular structure and said tubular structure is cut on one side only and flared, making said branches 204 or 205 so as to obtain only one side of the supporting structure 2 to be connected with an opposite side made similarly.

In accordance with an alternative embodiment, said supporting structure 2 is obtained from a tubular structure and said tubular structure is cut on both sides and each side is flared and forming said branches 204 and 205.

In accordance with an alternative embodiment, said branches 204 or 205 for each end 202, 203 of the supporting structure 2 are between 3 and 10 in number.

In accordance with an alternative embodiment, said branches 204 or 205 for each end 202, 203 of the supporting structure 2 are elastically connected to the central portion 201 and in the folded position are elastically crimped in a releasable manner to form a tube shape again.

In accordance with an alternative embodiment, each free end of the branch 204, 205 is folded and shaped to form a spoon-shaped tip 206 so as to be atraumatic and adapted to be guided inside a catheter of an insertion device.

In accordance with an alternative embodiment, said at least one membrane 8 is spread on the branches 204 or 205 only on one end 202 OR 203 of the supporting structure 2.

In accordance with an alternative embodiment, said at least one membrane 8 are two membranes 8, and each membrane 8 is spread over the branches 204 and 205 of each respective end 202 and 203 of the supporting structure 2.

In accordance with an alternative embodiment, at least one branch of said branches 204, 205 comprises a ring or petal shape.

In accordance with an alternative embodiment, said supporting structure 2 is obtained from a tubular structure and said tubular structure is cut so as to obtain a metal wire frame of petal-edge shape.

In accordance with an alternative embodiment, said occluder device 1 comprises a fastening element 207 for locking said branches 204, 205 in said unfolded or lying position.

In accordance with an alternative embodiment, said occluder device 1 comprises a fastening element 207; in which said fastening element 207 is screwed into a contracted position to lock said branches 204, 205 in said unfolded or lying position by means of a screw-nut coupling.

In accordance with an alternative embodiment, said occluder device 1 comprises a fastening element 207; in which said fastening element 207 is locked in a contracted position to lock said branches 204, 205 in said unfolded or lying position by means of a suture filament or a metal wire.

In accordance with an alternative embodiment, said occluder device 1 comprises a fastening element 207 arranged through said central portion 201.

In accordance with an alternative embodiment, said occluder device 1 comprises a fastening element 207 to provide a retention or anchoring force to the septal tissue 7, 100, 104.

In accordance with an alternative embodiment, said occlusion device 1 comprises a fastening element 207 to provide an attachment for a release system adapted to deliver said occlusion device 1 in situ.

In accordance with an alternative embodiment, said occluder device 1 comprises a fastening element 207, said fastening element 207 comprises ball ends 208.

In accordance with an alternative embodiment, said occluder device 1 comprises a fastening element 207, said fastening element 207 comprises flat ends 208.

In accordance with an alternative embodiment, said occluder device 1 comprises a fastening element 207 for elastically influencing said branches 204, 205 in said unfolded or lying position.

In accordance with an alternative embodiment, said occluder device 1 comprises a fastening element 207; in which said fastening element 207 is elastically influenced in a contracted position to elastically influence said branches 204, 205 in said unfolded or lying position.

In accordance with an alternative embodiment, said occluder device 1 comprises a fastening element 207; in which said fastening element 207 is elastically influenced in a contracted position to elastically influence said branches 204, 205 in said unfolded or lying position by a spring.

In accordance with an alternative embodiment, said occluder device 1 comprises a fastening element 207; in which said fastener 207 is magnetically influenced in a contracted position to magnetically influence said branches 204, 205 in said unfolded or lying position.

The present invention further relates to a method for crossing an occluder device 1, comprising the following steps:

> providing an occluder device 1 according to any one of the embodiments described above;
>
> actively engaging an external device 108, for example a catheter, to the membrane 8;
>
> elastically deforming the at least one slit 21, creating a passage lumen 27;
>
> crossing the occluder device 1 with said external device 108.

In accordance with an embodiment variant of said method, the further steps are included of:

> retracting the external device 108, allowing the membrane 8 to close in the original condition thereof.

In accordance with an embodiment, said occluder device 1 comprises at least one slit 21. Said slit 21 extends at least partially outside the central portion 201 and alternatively > moves away from the central portion 201
>
> or
>
> at least partially bypasses said central portion 201 remaining outside thereof.

In accordance with an embodiment, said at least one slit 21 extends at least in part next to said distal or proximal branches 204, 205, so that, when actively engaged by an external device 108, this crosses the membrane 8 outside the central portion 201.

In accordance with an embodiment, said distal and/or proximal branches 204, 205 extend over a branch area and said membrane 8 extends to at least partially cover this branch area.

In accordance with an embodiment, said central portion 201 avoids creating a passage lumen therein capable of letting said external device 108 pass.

In accordance with an embodiment, said supporting structure 2 is made of a less elastic material with respect to the material of said membrane 8. For example, said supporting structure is made of metallic material. For example, said supporting structure is made of metallic super elastic material.

In accordance with an embodiment, said membrane 8 comprises at least one bridge or occlusion bridge 15.

Said at least one bridge 15 comprises an elongated bridge body having opposite bridge connecting portions 16, 17 and opposite bridge edges coinciding with slit edges 18.

Each of said slit edges 18 delimits at least one slit 21 present in said membrane 8.

Both of said opposite bridge connecting portions 16, 17 are directly or indirectly connected with said supporting structure 2.

In accordance with an embodiment, when said membrane 8 is in a relaxed condition, said membrane 8 is flat in shape and the at least one bridge 15 is lying flat on said supporting structure 2.

In accordance with an embodiment, when said membrane 8 is in a relaxed condition, said membrane 8 is flat in shape and the at least one bridge 15 is lying tensioned on said supporting structure 2.

In accordance with an embodiment, said at least one bridge 15 is made of deformable elastic material configured so as to extend when an external device 108 passes through the at least one slit 21.

In accordance with an embodiment, said membrane 8 comprises at least two bridges or occlusion bridges 15.

Said at least two bridges 15 each comprise an elongated bridge body having opposite bridge connecting portions 16, 17 and opposite bridge edges coinciding with slit edges 18.

Each of said slit edges 18 delimits with the slit edge 18 of the adjacent bridge at least one slit 21 present in said membrane 8.

For each bridge 15, both of said opposite bridge connecting portions 16, 17 are directly or indirectly connected with said supporting structure 2.

In accordance with an embodiment, when said membrane 8 is in a relaxed condition, said membrane 8 is flat in shape and the at least two bridges 15 are flat on said supporting structure 2.

In accordance with an embodiment, when said membrane 8 is in a relaxed condition, said membrane 8 is flat in shape and the at least two bridges 15 are lying tensioned on said supporting structure 2.

In accordance with an embodiment, said at least two bridges 15 are made of deformable elastic material configured so as to extend when an external device 108 passes through the at least one slit 21.

LIST OF REFERENCES

1 occluder device
2 supporting structure
3 central supporting structure portion
4 septum lumen
5 supporting structure periphery
6 structure central opening
7 septum
8 membrane or diaphragm
9 first compartment
10 second compartment
11 membrane body
12 membrane periphery
14 membrane center
15 bridge
16 bridge connecting membrane periphery portion
17 bridge connecting membrane periphery portion
18 slit edges
19 dovetail joint
20 membrane body structure
21 membrane slit or cut
22 membrane vertex
23 membrane thickness
27 passage lumen created with the slit by the elastic extension of the membrane
29 membrane body rib
30 membrane strip
31 membrane magnets
103 heart
104 ventricular septum
105 right ventricle
106 left ventricle
107 defect or opening
108 external device
201 central supporting structure portion
202 distal supporting structure end
203 proximal supporting structure end
204 distal branches
205 proximal branches
206 branch tip or branching enlarged in the shape of a spoon
207 branch stop element in unfolded position
208 stop element ball ends

12

The invention claimed is:

1. An occluder device comprising:
a supporting structure, said supporting structure comprising a central portion having a distal end and a proximal end;
said supporting structure comprising distal branches extending away from said distal end of the central portion;
said supporting structure comprising proximal branches extending away from said proximal end of the central portion;
said proximal branches and distal branches being bendable to anchor the occluder device in a septum of a heart;
said occluder device further comprising at least one membrane;
said at least one membrane comprises a membrane body connected to at least one of the distal branches or the proximal branches;
when the distal branches and the proximal branches are in an unfolded or lying position, said at least one membrane has a closed position where the at least one membrane is in a configuration which provides maximum occlusion to the supporting structure; and
said at least one membrane comprising at least one slit, which, when actively engaged by an external device the at least one membrane deforms the at least one slit which extends elastically, creating a passage lumen for said external device, wherein the at least one slit is spaced from the central portion and is located between a pair of adjacent branches of the proximal branches or the distal branches of which the at least one membrane is connected to, such that, when actively engaged by said external device, the external device crosses the at least one membrane outside the central portion.

2. The occluder device of claim 1, wherein said at least one slit does not extend over the central portion.

3. The occluder device of claim 1, wherein at least one of said distal branches or said proximal branches extend over a branch area and said at least one membrane extends to at least partially cover this branch area.

4. The occluder device of claim 1, wherein said central portion avoids creating a passage lumen therein capable of letting said external device pass therethrough.

5. The occluder device of claim 1, wherein said distal branches and said proximal branches move from a folded position, where the distal branches and the proximal branches are grouped near the central portion or a virtual extension thereof, to an unfolded, or lying, position, where the distal branches and the proximal branches extend away from said central portion, and vice versa; and said distal branches and said proximal branches are adapted to anchor the occluder device to the septum of the heart when the supporting structure crosses a septum defect and said distal branches and said proximal branches are in an open or lying position.

6. The occluder device of claim 1, wherein said central portion is a tubular portion.

7. The occluder device of claim 1, wherein said central portion defines a central axis and said distal branches and said proximal branches are configured to be arranged orthogonally with respect to the central axis when the supporting structure is in an unfolded or extended configuration and outside of a patient's body.

8. The occluder device of claim 1, wherein said distal branches or said proximal branches are equidistant from each other.

9. The occluder device of claim 1, wherein some of said distal branches or said proximal branches have different lengths.

10. The occluder device of claim 1, wherein said distal branches or said proximal branches are uniformly distributed around a circumference.

11. The occluder device of claim 1, wherein said distal branches or said proximal branches are unevenly distributed around a circumference.

12. The occluder device of claim 1, wherein each proximal branch is aligned with a corresponding distal branch when the occluder device is in a position to lock an interposed tissue.

13. The occluder device of claim 1, wherein said at least one membrane has an external membrane periphery and wherein said at least one slit extends from the external membrane periphery in a direction converging to said central portion.

14. The occluder device of claim 1, wherein said at least one slit extends along a circumferential path.

15. The occluder device of claim 1, wherein said at least one slit is a notch in the membrane body.

16. The occluder device of claim 1, wherein said at least one slit are at least two slits.

17. The occluder device of claim 16, wherein said at least two slits extend parallel to each other.

18. The occluder device of claim 1, wherein said at least one slit are a plurality of slits uniformly distributed around said central portion.

19. An occluder device comprising:
a supporting structure comprising:
  a central portion extending between a first end and a second end;
  a plurality of first branches extending away from the first end of the central portion; and
  a plurality of second branches extending away from the second end of the central portion,
  wherein the plurality of first branches and the plurality of second branches are configured to anchor the occluder device in a septum of a heart, in use; and
a membrane coupled to at least one of the plurality of first branches or the plurality of second branches, the membrane comprising a slit, which, when actively engaged by an external device, the membrane is configured to deform at the slit to create a passage lumen for the external device, wherein the slit is located between a pair of adjacent branches of the plurality of first branches or the plurality of second branches of which the membrane is coupled to, wherein the slit does not extend over the central portion, and wherein the passage lumen allows the external device to cross both the membrane and the septum of the heart.

* * * * *